(12) United States Patent
Okumura et al.

(10) Patent No.: US 8,809,218 B2
(45) Date of Patent: Aug. 19, 2014

(54) ZEOLITE-PALLADIUM COMPLEX, METHOD FOR PRODUCING THE SAME, CATALYST CONTAINING THE COMPLEX, AND METHOD FOR PRODUCING A COUPLING COMPOUND BY USING THE CATALYST

(75) Inventors: Kazu Okumura, Tottori (JP); Miki Niwa, Tottori (JP); Hirosuke Matsui, Tottori (JP); Yoshinori Enmi, Tottori (JP); Takuya Tomiyama, Tottori (JP); Shizuyo Okuda, Tottori (JP)

(73) Assignee: National University Corporation Tottori University, Tottori (JP)

( * ) Notice: Subject to any disclaimer, the term of this patent is extended or adjusted under 35 U.S.C. 154(b) by 58 days.

(21) Appl. No.: 13/203,083

(22) PCT Filed: Feb. 23, 2010

(86) PCT No.: PCT/JP2010/052739
§ 371 (c)(1), (2), (4) Date: Aug. 24, 2011

(87) PCT Pub. No.: WO2010/098310
PCT Pub. Date: Sep. 2, 2010

(65) Prior Publication Data
US 2012/0059191 A1 Mar. 8, 2012

(30) Foreign Application Priority Data

Feb. 24, 2009 (JP) ................................. 2009-041547
Sep. 7, 2009 (JP) ................................. 2009-205487

(51) Int. Cl.
*B01J 21/00* (2006.01)
*B01J 29/00* (2006.01)
*C07C 17/00* (2006.01)
*C07C 1/32* (2006.01)

(Continued)

(52) U.S. Cl.
CPC ............... *B01J 35/002* (2013.01); *C07C 1/321* (2013.01); *C07C 2523/44* (2013.01); *C07C 45/68* (2013.01); *B01J 29/126* (2013.01); *C07C 41/30* (2013.01); *C07C 209/68* (2013.01); *C01B 39/24* (2013.01); *C07C 49/796* (2013.01); *B01J 37/18* (2013.01); *B01J 37/30* (2013.01); *C07C 2529/08* (2013.01); *C07C 67/343* (2013.01); *C07C 1/26* (2013.01)
USPC ............................................ 502/74; 570/171

(58) Field of Classification Search
None
See application file for complete search history.

(56) References Cited

FOREIGN PATENT DOCUMENTS

JP 2010-069415 2/2010

OTHER PUBLICATIONS

Artok, Levent and Hatice Bulut. "Heterogeneous Suzuki reactions catalyzed by Pd(0)-Y zeolite." *Tetrahedron Letters*. No. 45 (2004). pp. 3881-3884.

(Continued)

*Primary Examiner* — Clinton Brooks
(74) *Attorney, Agent, or Firm* — Stein IP, LLC

(57) ABSTRACT

There is provided a substance having much higher catalytic activity for a Suzuki-Miyaura coupling reaction than conventional heterogenous catalysts. The present invention provides a zeolite-palladium complex including USY-zeolite and Pd supported on the USY-zeolite, the Pd having a Pd—Pd coordination number of 4 or less and an oxidation number of 0.5 or less.

5 Claims, 18 Drawing Sheets

(51) Int. Cl.
  C07C 45/68    (2006.01)
  B01J 29/12    (2006.01)
  C07C 41/30    (2006.01)
  C07C 209/68   (2006.01)
  C01B 39/24    (2006.01)
  C07C 49/796   (2006.01)
  B01J 37/18    (2006.01)
  B01J 35/00    (2006.01)
  B01J 37/30    (2006.01)
  C07C 67/343   (2006.01)
  C07C 1/26     (2006.01)

(56) References Cited

OTHER PUBLICATIONS

Bulut, Hatice, et al. "Suzuki cross-coupling reactions of aryl halides with arylboronic acids catalysed by Pd(II)-NaY zeolite." *Tetrahedron Letters*. No. 44 (2003). pp. 289-291.

Diallo, Abdou Khadri, et al. "'Homeopathic' Catalytic Activity and Atom-Leaching Mechanism in Miyaura-Suzuki Reactions under Ambient Conditions with Precise Dendrimer-Stabilized Pd Nanoparticles." *Angew. Chem. Int. Ed.*, vol. 46, No. 45 (2007). pp. 8644-8648.

Durgun, Gülay, et al. "Pd-loaded NaY zeolite as a highly active catalyst for ligandless Suzuki-Miyaura reactions of aryl halides at low Pd loadings under aerobic conditions." *Journal of Molecular Catalysts A: Chemical*. No. 278 (2007). pp. 189-199.

Hagiwara, Hisahiro, et al. "Environmentally benign Suzuki-Miyaura coupling catalyzed by Pd supported on alumina by an ionic liquid." *The Chemical Society of Japan, Proceeding*. vol. 87, No. 2 (2007). p. 1055. (In Japanese with English abstract).

Hagiwara. Hisahiro, et al. "Supported ionic liquid catalyst (Pd-SILC) for highly efficient and recyclable Suzuki-Miyaura reaction." *Chem. Commun*. (2007). pp. 2838-2840.

Jiang, Nan and Arthur J. Ragauskas. "Environmentally friendly synthesis of biaryls: Suzuki reaction of aryl bromides in water at low catalyst loadings." *Tetrahedron Letters*. vol. 47 (2006). pp. 197-200.

Kudo, Daisuke, et al. "An Efficient Heterogeneous Pd Catalyst for the Suzuko Coupling: $Pd/Al_2O_{3s}$." *Chemistry Letters*. vol. 36, No. 7 (2007). pp. 918-919.

Li, Shenghai, et al. "Guanidine/$Pd(OAc)_2$-Catalyzed Room Temperature Suzuki Cross-Coupling Reaction in Aqueous Media under Aerobic Conditions." *J. Org. Chem*. No. 72 (2007). pp. 4067-4072.

Maruyama, R., et al. "A Suzuki coupling reaction by a Pd-supported catalyst in an aqueous solution." *Catalyst Symposium, Symposium A Proceeding*. vol. 92 (2003). p. 137. (In Japanese with English Abstract).

Mori, Koshuke, et al. "Controlled Synthesis of Hydroxyapatite-Supported Palladium Complexes as Highly Efficient Heterogeneous Catalysts." *J. Am. Chem. Soc*. vol. 124. (2002) pp. 11572-11573.

Okumura, Kazu, et al. "Generation of the active Pd cluster catalyst in the Suzuki-Miyaura reactions: Effect of the activation with H2 studied by means of quick XAFS." *Journal of Catalysis*. vol. 265 *(2009). pp. 89-98.

Okumura, Kazu, et al. "In-Situ QXAFS Studies on the Dynamic Coalescence and Dispersion Processes of Pd in the USY Zeolite." *J. Phys. Chem. C*. vol. 111 (2007). pp. 14426-14432.

Okumura, Kazu, et al. "Stepwise Growth of Pd Clusters in USY Zeolite at Room Temperature Analyzed by QXAFS." *J. Phys. Chem. C*. vol. 112 (2008). pp. 16740-16747.

Okumura, Kazu, et al. "sono Ba Kangenho ni yori Keisei sareta Pd Cluster Shokubai ni yoru Suzuki-Miyaura Coupling Hanno." *Shokubai*. (2009). pp. 126-128.

Schneider, Sabine K., et al. "Pyridin-, Quinolin- and Acridinylidene Palladium Carbene Complexes as Highly Efficient C-C Coupling Catalysts." *Adv. Synth. Catal*. vol. 348 (2006). pp. 1862-1873.

Shimizu, Kenichi, et al. "A cross-coupling reaction by a Pd-supported FSM-16 Catalyst." *Catalyst*. vol. 46, No. 6 (2004). pp. 533-535.

Takemoto, Toshihide, et al. "Highly efficient Suzuki-Miyaura coupling reactions catalyzed by bis(oxazolinyl)phenyl-Pd(II) complex." *Tetrahedron Letters*. vol. 48 (2007). pp. 3397-3401.

Wolfe, John P., et al. "Highly Active Palladium Catalysts for Suzuki Coupling Reactions." *J. Am. Chem. Soc*. vol. 1212 (1999). pp. 9550-9561.

International Search Report for PCT/JP2010/052739 mailed Jun. 29, 2010.

(a) Before steaming treatment
(b) 773 K, 1 hour
(c) 823 K, 10 hours
(d) 873 K, 1 hour

ZEOLITE-PALLADIUM COMPLEX, METHOD FOR PRODUCING THE SAME, CATALYST CONTAINING THE COMPLEX, AND METHOD FOR PRODUCING A COUPLING COMPOUND BY USING THE CATALYST

CROSS-REFERENCE TO RELATED APPLICATIONS

This application is a National Stage of PCT International Patent Application No. PCT/JP2010/052739, filed Feb. 23, 2010, which claims the benefit of Japanese Patent Application Nos. 2009-041547 and 2009-205487, filed Feb. 24, 2009 and Sep. 7, 2009, respectively, in the Japanese Patent Office, the disclosures of which are incorporated herein by reference.

BACKGROUND OF THE INVENTION

1. Field of the Invention

The present invention relates to zeolite-palladium complexes, methods for producing the complex, catalysts containing the complex, and methods for producing a coupling compound by using the catalyst. In addition, the present invention relates to a precursor of the zeolite-palladium complex, and NH4+-containing USY-zeolite and H—USY-zeolite for producing the precursor.

2. Description of the Related Art

A Suzuki-Miyaura coupling reaction as exemplified in the following chemical equation is a coupling reaction of an aromatic boron compound with aryl halide, etc. The reaction is an extremely useful tool for synthesizing biologically active substances such as a pharmaceutical and source materials for functional molecules such as an organic EL.

[Chemical Formula 1]

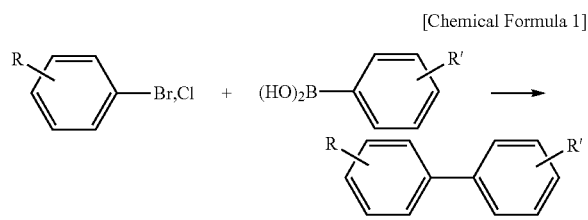

Suzuki-Miyaura Coupling Reaction

The aromatic boron compound which is used as a source material for the Suzuki-Miyaura coupling reaction only reacts with a functional group (halide) of interest, is also stable in water and air, and can be preserved as a crystalline solid for a long term. Further, borate as a byproduct of the above Suzuki-Miyaura coupling reaction does not possess toxicity, and can be even readily separated from a target substance by washing with water. Because of these characteristics, the Suzuki-Miyaura coupling reaction has been widely applied from a laboratory level to an industrial scale.

In one hand, a catalyst having a conventional organometallic compound which is used as a catalyst for the Suzuki-Miyaura coupling reaction has high reactivity, and is thus applicable for various reactions. However, there is a problem that the catalyst reacts with those other than a functional group which is intended to be reacted. In contrast, a palladium catalyst supported onto zeolite is useful for various catalytic reactions such as NCL reduction, catalytic combustion, and organic synthesis. However, the structure of a Pd cluster formed in zeolite pores and the formation process thereof have not been fully investigated (Non-Patent Literature 1).

For example, Non-Patent Literature 2 describes that $Pd(NH_3)_4^{2+}$-supported NaY-zeolite has been found out to be a high-activity catalyst precursor for a Suzuki-Miyaura (SM) reaction of aryl bromide or aryl chloride with a phenylboronic acid derivative in the air under a low Pd concentration. In addition, this literature also describes that aryl bromide and arylboronic acid are effectively coupled in an aqueous mixture (1/1) of pure water and N,N-dimethylformamide within a few minutes at a turnover frequency (TOF) of $4 \times 10^5 h^{-1}$, and that the presence of a small amount of water is critical to achieve a reaction with chloroarene.

In addition, Non-Patent Literature 3 describes that for synthesis of biaryl derivatives obtained by a Suzuki cross-coupling between aryl bromides and arylboronic acids, a heterogenous catalyst of Pd(0)-Y-zeolite (I) has been used without addition of a ligand, and that a target substance has been produced at a high yield. In addition, this literature also describes that $Na_2CO_3$ or $Cs_2CO_3$ has been optimal for a base coexisted and $DMF/H_2O$ or $DMA/H_2O$ has been optimal for a solvent, and that coexistence of $H_2O$ in the solvent system has been required. Further, this literature also describes that, for example, 4-cyanobiphenyl has been produced at a yield of 100% by reacting 4-CN-PhBr with $PhB(OH)_2$ under the presence of I and $Na_2CO_3$ in a solvent of $DMF/H_2O$ at room temperature, and that the catalyst can be used repeatedly.

Further, Non-Patent Literature 4 describes that when a Pd(II)-NaY-zeolite catalyst has been prepared by carrying out calcination of NaY-zeolite impregnated in $Pd(NH_3)_4Cl_2$ under oxygen stream, a corresponding biaryl has been efficiently synthesized by performing a captioned cross-coupling reaction under the presence of a base in a mixed solvent of DMF/water by using this catalyst. In addition, this literature also describes that the best result has been obtained in the case of use of sodium carbonate or potassium carbonate as a base and a 1:1 mixture of DMF and water as a solvent, and that the catalyst could be readily recovered by filtering the reaction solution and be repeatedly used.

In addition to the above, as disclosed in Non-Patent Literatures 5 to 16, methods for a Suzuki coupling reaction utilizing various Pd catalysts have been reported. In addition, among the literatures, there is a literature reporting that the TON (turnover number) for a catalyst system is approximately one million.

PRIOR ART REFERENCE

Patent Document

[Non-Patent Literature 1] K. Okumura, K., Kato, T., Sanada, M., and Niwa, J. Phys. Chem. C, 111, 14426 (2007).
[Non-Patent Literature 2] DURGUN Guelay, AKSIN Oezge, ARTOK Levent, J. Mol. Catal. A, 278, (2007) 179.
[Non-Patent Literature 3] ARTOK L and BULUT H, Tetrahedron Letters, 45 (2004), 3881-3884.
[Non-Patent Literature 4] BULUT H, ARTOK L, and YILMAZ S, Tetrahedron Letters, 44 (2003), 289-291.
[Non-Patent Literature 5] MARUYAMA R, KANNO T, SHIMIZU K, KODAMA T, and KITAYAMA Y, Catalyst Symposium, Symposium A Proceeding, Vol. 92nd, Page. 137, (2003 Sep. 18).
[Non-Patent Literature 6] MORI K. YAMAGUCHI K. HARA T, MIZUGAKI T. EBITANI K. and KANEDA K, J. Am. Chem. Soc., Vol. 124, No. 39, Page 11572-11573 (2002 Oct 2).

[Non-Patent Literature 7] KUDO Daisuke, MASUI Yoichi, and ONAKA Makoto, Chem. Lett., Vol. 36, No. 7, Page 918-919 (2007).

[Non-Patent Literature 8] HAGIWARA Hisahiro, KO Keon Hyeok, HOSHI Takashi, and SUZUKI Toshio, Chem. Commun., No. 27, Page 2838-2840 (2007 Jul. 19).

[Non-Patent Literature 9] HAGIWARA H, KO Keon Hyeok, HOSHI T, and SUZUKI T, The Chemical Society of Japan, Proceeding, Vol. 87, No. 2, Page 1055 (2007 Mar. 12).

[Non-Patent Literature 10] SHIMIZU K, KOIZUMI S, KODAMA T, and KITAYAMA Y, SHOKUBAI (Catalyst), Vol. 46, No. 6, Page 533-535 (2004 Sep. 10).

[Non-Patent Literature 11] TAKEMOTO Toshihide, IWASA Seiji, HAMADA Hiroshi, SHIBATOMI Kazutaka, KAMEYAMA Masayuki, MOTOYAMA Yukihiro, and NISHIYAMA Hisao, Tetrahedron Lett., Vol. 48, No. 19, Page 3397-3401 (2007 May 7).

[Non-Patent Literature 12] JIANG Nan and RAGAUSKAS Arthur J., Tetrahedron Lett., Vol. 47, No. 2, Page 197-200 (2006 Jan. 9).

[Non-Patent Literature 13] WOLFE J P, SINGER R A, YANG B H, and BUCHWALD S L, J. Am. Chem. Soc., Vol. 121, No. 41, Page 9550-9561 (1999 Oct. 20).

[Non-Patent Literature 14] SCHNEIDER Sabine K., HERRMANN Wolfgang A., ROEMBKE Patric, JULIUS Gerrit R., and RAUBENHEIMER Helgard G, Adv. Synth. Catal., Vol. 348, No. 14, Page 1862-1873 (2006 September).

[Non-Patent Literature 15] LI Shenghai, ZHANG Suobo, LIN Yingjie, and CAO Jungang, J. Org. Chem., Vol. 72, No. 11, Page 4067-4072 (2007 May 25).

[Non-Patent Literature 16] DIALLO Abdou Khadri, ORNELAS Catia, RUIZ ARANZAES Jaime, ASTRUC Didier, and SALMON Lionel, Angew. Chem. Int. Ed., Vol. 46, No. 45, Page 8644-8648 (2007 December).

SUMMARY OF THE INVENTION

However, conventional techniques as described in the above literatures have a room for improvement in the following points.

First, a palladium catalyst supported onto zeolite as described in Non-Patent Literature 1 is useful for various catalytic reactions such as NO selective reduction, catalytic combustion, organic synthesis. However, there has been a room for improvement in an aspect of activity for a Suzuki-Miyaura coupling reaction. In addition, this literature has not fully investigated the structure of a Pd cluster formed in zeolite pores and the formation process thereof. Accordingly, how to form the Pd cluster in the zeolite pores and what kinds of structure of the Pd cluster have not been revealed to be able to easily prepare a catalyst exhibiting high activity, from a viewpoint of total ability of the catalytic activity evaluated in the Suzuki-Miyaura coupling reaction for a TON, a TOF, or a yield.

Second, a catalyst as described in Non-Patent Literatures 2 to 4 is set forth as TOF=120,000 h$^{-1}$ at the time of 90% yield in an experiment using, for example, bromobenzene (J. Mol. Catal. A, 278, (2007) 179, Table 2, entry 11). However, the TOF value largely differs depending on at which time point after the reaction initiation the TOF is calculated. Thus, it is not accurate to evaluate the activity as excellent determined only simply by the TOF. Because of this, in respect to the catalyst as described in Non-Patent Literatures 2 to 4, there has been a room for further improvement in the total ability of the catalytic activity estimated by the TON, the TOF, or the yield.

Third, catalysts as described in Non-Patent Literatures 5 to 16 are illustrated, including a catalyst using ion liquid, a heterogeneous catalyst using a catalyst having a complicated phosphine ligand, and a homogeneous catalyst which is reacted in a solution. It has been reported that some heterogenous catalysts exhibit high activity. However, a preparation method for immobilizing a catalyst is complicated for the catalyst using ion liquid and the heterogenous catalyst using a catalyst having a complicated phosphine ligand. Accordingly, there has been a room for further improvement in aspects of the productivity and the cost. In addition, although some heterogenous catalysts exhibit high activity, this is simply because the excessive amount of Pd utilized in these heterogenous catalysts causes the high activity. Thus, there has been a room for further improvement in an aspect of the total ability of the catalytic activity estimated by the TOF and TON.

The present invention has been invented in light of the above situations, and provides a substance having much higher catalytic activity for a Suzuki-Miyaura coupling reaction than conventional heterogenous catalysts.

The present invention provides a zeolite-palladium complex including USY-zeolite and Pd supported on the USY-zeolite, the Pd having a Pd—Pd coordination number of 4 or less and an oxidation number of 0.5 or less.

As a result of intensive research, the present inventors have found that a substance has been obtained by H$_2$ bubbling over ultrastable Y-zeolite (hereinafter, referred to as the "USY-zeolite") on which a palladium salt is supported, in xylene or toluene at a temperature of 80 to 140° C. under an H$_2$ partial pressure of 1 to 30%, and that the substance has extremely high catalytic activity for a Suzuki-Miyaura coupling reaction. Subsequently, as a result of further research to identify this substance, the substance has been found to be highly dispersed on the USY-zeolite in a single atom or in a microcluster state of Pd having a Pd—Pd coordination number of 4 or less and having an oxidation number of 0.5 or less. Finally, the inventors have completed the present invention.

For a comparison, the present inventors have carried out H$_2$ bubbling under the similar conditions using zeolite other than the USY-zeolite. Then, the catalytic activity of the resulting substance has been much lower than the case of using the USY-zeolite. By considering this comparative experiment, the phenomenon that a substance having high catalytic activity is yielded by H$_2$ bubbling has been found to be a USY-zeolite-specific one. A principle is not necessarily clear that a substance having high catalytic activity is yielded by using USY-zeolite. However, the USY-zeolite has strong acid sites generated by dealumination of the USY-zeolite, and these strong acid sites contribute to stabilization of Pd in a single atom or in a microcluster state. Consequently, the presumed reason is that Pd is highly dispersed and is supported on the USY-zeolite.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
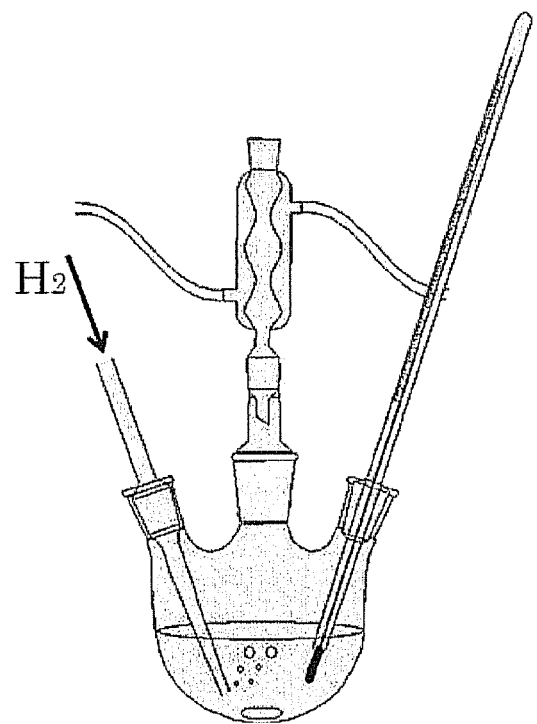
FIG. 1 shows a three-neck flask to carry out H$_2$ bubbling and a Suzuki-Miyaura coupling reaction.

Hereinafter, embodiments of the present invention are illustrated.

1. Zeolite-Palladium Complex

A zeolite-palladium complex of an embodiment of the present invention includes USY-zeolite and Pd supported on the USY-zeolite, the Pd having a Pd—Pd coordination number (hereinafter, simply referred to as the "coordination number") of 4 or less and an oxidation number of 0.5 or less.

1-1. USY-Zeolite

USY-zeolite refers to a kind of FAU-zeolite. In the FAU-zeolite, there exist what is called supercages of nearly spherical spaces having a diameter of 1.3 nm. This space possesses four windows having a diameter of 0.74 nm. A supercage is linked to four contiguous supercages via these windows. A commercially available one (e.g., those manufactured by Tosoh Corporation) can be used as USY-zeolite. The USY-zeolite may be prepared using commercially available NaY-zeolite (e.g., those manufactured by Tosoh Corporation, those manufactured by JGC Catalysts and Chemicals Ltd.) by performing ion exchange with an ammonium ion, followed by high-temperature steaming treatment to carry out dealumination.

1-2. Pd

Pd is supported on USY-zeolite. This Pd has a Pd—Pd coordination numbe of 4 or less and an oxidation number of 0.5 or less. For a zeolite-palladium complex of an embodiment of the present invention, Pd having such a small oxidation number is highly dispersed, and thus seems to possess high catalytic activity.

When Pd completely becomes an atomic state, the coordination number is 0. When Pd becomes a cluster having four atoms, the coordination number is about 3. In addition, when Pd becomes a cluster having six atoms, the coordination number is about 4. Preferably, the coordination number is between 0 and 3. This is because the catalytic activity of a complex of this embodiment is particularly elevated in this case.

The coordination number can be determined by analyzing data of X-ray absorption spectra (EXAFS). This method is a method for investigating what distance, how many atoms (coordination number), and what kind of atom is present in the surrounding of a certain particular Pd atom within a distance of about 4 angstroms or less. The coordination number can be specifically determined by the following procedure. (1) Pd K-edge EXAFS is determined by using, for example, SPring-8 BL01B1. (2) Vibrations are extracted from the resulting spectra by a cubic spline method, and are subjected to Fourier transforms within a range between 25 and 130 $nm^{-1}$, followed by inverse Fourier transforms within a range between 0.1 and 0.3 nm. (3) The spectra which have been inverse Fourier transformed into k-space are analyzed within a range between 25 and 130 $nm^{-1}$ by a curve-fitting method. (4) For the structural analysis, PdO, CdS, and Pd foil are used as standard samples for Pd—O, Pd—Al, and Pd—Pd, respectively. The analysis can use, for example, Rex2000 (ver. 2.5) developed by Rigaku, Inc.

The oxidation number of Pd is 0.5 or less, and preferably between 0 and 0.3. This is because the catalytic activity of Pd is particularly elevated when the oxidation number of Pd is within this range. The oxidation number of Pd can be calculated by Pd $L_3$-edge XANES analysis.

2. Catalyst Containing Zeolite-Palladium Complex

As described above, the above zeolite-palladium complex functions as a catalyst because it has a property of promoting a Suzuki-Miyaura coupling reaction. Accordingly, the present invention provides a catalyst containing a zeolite-palladium complex. This catalyst has, but is not limited to, a property of promoting a Suzuki-Miyaura coupling reaction, and is also considered to promote other chemical reactions which proceed in, for example, xylene or toluene. The foregoing catalyst is a heterogenous catalyst from a viewpoint of use as a solid state. In addition, the foregoing catalyst is a catalyst for a Suzuki-Miyaura coupling reaction from a viewpoint that it catalyzes the Suzuki-Miyaura coupling reaction.

3. Method for Producing Zeolite-Palladium Complex

A method for producing a zeolite-palladium complex of an embodiment of the present invention includes the steps of: obtaining a zeolite-palladium complex precursor by mixing $NH_4^+$-containing USY-zeolite with a palladium ammonium salt; and carrying out $H_2$ bubbling over the resulting precursor in xylene or toluene at a temperature between 20° C. and 170° C. under an $H_2$ partial pressure of 1 to 30%. In addition, the above method for producing a zeolite-palladium complex is not limited to methods as described herein, but the complex can be produced by any method.

3-1. $NH_4^+$-Containing USY-Zeolite $NH_4^+$-containing USY-zeolite refers to USY-zeolite which contains $NH_4^+$. Mixing $NH_4^+$-containing USY-zeolite with a palladium ammonium salt allows palladium to be supported on the zeolite in a highly dispersed state and yields a zeolite-palladium complex precursor having high catalytic performance.

The $NH_4^+$ content is preferably, but is not particularly limited to, between 0.15 and 1.3 mol/kg, more preferably between 0.3 and 1.1 mol/kg, and further preferably between 0.4 and 1 mol/kg. As a result of intensive research, the present inventors have found that the amount of $NH_4^+$ in the $NH_4^+$-containing USY-zeolite imparts a large influence on dispersibility of Pd, and that in the case of the above value, the catalytic activity of the zeolite-palladium complex is particularly elevated. The amount of $NH_4^+$ in the $NH_4^+$-containing USY-zeolite can be determined by a temperature-programmed desorption method (TPD). Heating $NH_4^+$-containing USY-zeolite detaches $NH_4^+$ as $NH_3$. Accordingly, the measurement of an amount of the detached $NH_3$ can determine the amount of $NH_4^+$ contained in the zeolite.

As an example, $NH_4^+$-containing USY-zeolite can be produced by ion exchange of H—USY-zeolite with an ammonium salt (e.g., ammonium nitrate), followed by calcination. The higher the calcination temperature is, the more the amount of $NH_4^+$ decreases. Thus, changing the calcination temperature can adjust the amount of $NH_4^+$. The calcination temperature is preferably between 150 and 350° C. This is because calcination using such a temperature readily results in a value within the above preferable range of the amount of $NH_4^+$. The calcination temperature is, for example, 150, 175, 200, 225, 250, 275, 300, 325, or 350° C. The range of the calcination temperature may be within a range between any two of the values designated above. The calcination time is preferably, for example, from 1 to 20 hours, more preferably from 2 to 10 hours, and further preferably from 3 to 5 hours. This is because about such time allows the amount of $NH_4^+$ to partially detach and to appropriately remain.

H—USY-zeolite for producing $NH_4^+$-containing USY-zeolite can be produced by performing steaming treatment for $NH_4$—Y-zeolite. The steaming treatment causes dealumination to generate strong acid sites. The present inventors have found that as the number of strong acid sites increase, the catalytic activity becomes higher. Specifically, when the amount of strong acid sites having ΔH of 130 to 145 kJ/mol (hereinafter, simply referred to as the "amount of strong acid sites") is 0.12 mol/kg or more, the catalytic activity is found to be markedly elevated. The lower limit of the amount of strong acid sites is preferably, for example, 0.15, 0.18, or 0.21 mol/kg. For example, the upper limit of the amount of strong acid sites is, but is not particularly limited to, 0.21, 0.25, 0.3, or 0.5 mol/kg or less. Any of the temperature, duration, and water vapor partial pressure of the steaming treatment is not particularly limited. The temperature of the steaming treatment is preferably between 475 and 600° C., and more preferably between 500 and 550° C. The duration of the steaming treatment is preferably between 5 and 17 hours, and more preferably between 8 and 12 hours. For example, the partial pressure of the steaming treatment is, but is not particularly limited to, 1%, 5%, 10%, 20%, 30%, 40%, or 50%. The partial pressure of the steaming treatment may be within a range between any two of the values designated above. A component other than water vapor preferably employs inert gas, and, for example, nitrogen or argon.

3-2. Palladium Ammonium Salt

A palladium ammonium salt used in a method of an embodiment of the present invention is preferably tetraammine palladium salt, and more preferably tetraammine palladium chloride ($Pd(NH_3)_4Cl_2$) or tetraammine palladium nitrate ($Pd(NH_3)_4(NO_3)_2$). This is because in the case of use of tetraammine palladium salt, the activity of the zeolite-palladium complex is much further higher than in the case of use of other palladium salts.

3-3. Precursor of Zeolite-Palladium Complex

Mixing $NH_4^+$-containing USY-zeolite with a palladium ammonium salt forms a zeolite-palladium complex precursor in which divalent palladium is supported on the USY-zeolite. The mixing method is not particularly limited as long as zeolite and the salt sufficiently mix. As an example, $NH_4^+$-containing USY-zeolite and a palladium ammonium salt are placed in the same container and are stirred at room temperature for 1 to 10 hours. Then, the mixture is filtered and dried to be able to yield a zeolite-palladium complex precursor. The zeolite-palladium complex precursor is referred to as the "precursor" in that palladium has not yet been reduced. By reducing Pd of the precursor by $H_2$ bubbling, a zeolite-palladium complex can be produced.

The supported amount of palladium is preferably, but is not particularly limited to, between 0.1 and 1 wt %, and more preferably between 0.2 and 0.7 wt %. This is because this level of the supported amount can keep the catalytic activity sufficiently high and keep usage of palladium sufficiently low, thereby lowering the manufacturing cost of the zeolite-palladium complex.

3-4. $H_2$ Bubbling

By carrying out $H_2$ bubbling over the above zeolite-palladium complex precursor in a solvent containing at least one of xylene and toluene at a temperature between 20° C. and 170° C. under an $H_2$ partial pressure of 1 to 30%, palladium is reduced to yield a zeolite-palladium complex having high catalytic activity.

3-4-1. Solvent for $H_2$ Bubbling $H_2$ bubbling is performed in a solvent containing at least one of xylene and toluene. This is because when xylene or toluene is employed as a solvent, reduced palladium is highly dispersed on zeolite. In the case of use of xylene, the degree of dispersion is particularly elevated. The xylene may be any of o-, m-, and p-xylene. This is because use of any xylene allows palladium to highly disperse. Examples of the solvent can include xylene alone, toluene alone, a mixture of xylene and toluene, and a mixture containing xylene, toluene, and a component other than them. When the component other than xylene and toluene is included, the percentage of xylene and toluene is preferably 20% by volume or more, 50% by volume or more, 60% by volume or more, 70% by volume or more, 80% by volume or more, 90% by volume or more, 95% by volume or more, or 99% by volume or more. This is because in the case of inclusion of a component other than xylene and toluene, inclusion of xylene or toluene enables palladium to highly disperse. In addition, the percentage of xylene is preferably 20% by volume or more, 50% by volume or more, 60% by volume or more, 70% by volume or more, 80% by volume or more, 90% by volume or more, 95% by volume or more, or 99% by volume or more. This is because inclusion of xylene allows palladium to particularly highly disperse.

3-4-2. Temperature of $H_2$ Bubbling

The temperature of $H_2$ bubbling is between 20° C. and 170° C. Palladium is readily reduced at a temperature of 80° C. or more. However, even if $H_2$ bubbling is carried out at a temperature between 20 and 80° C., the remaining hydrogen in the solvent reduces palladium by elevating a temperature to 80° C. or more after the bubbling. In view of this aspect, the temperature of $H_2$ bubbling is preferably 80° C. or more, more preferably 90° C. or more, and further preferably 100° C. or more. In addition, when the temperature of $H_2$ bubbling exceeds 170° C., a cluster of palladium rapidly grows. Hence, from a viewpoint that a microcluster of palladium having an atomic state or a coordination number of 4 or less is obtained by inhibiting growth of a palladium cluster, the temperature of $H_2$ bubbling is preferably 170° C. or less, and more preferably 160° C. or less, 150° C. or less, 140° C. or less, 130° C. or less, or 120° C. or less. From a viewpoint of inhibiting evaporation of a solvent, the upper limit of the temperature of $H_2$ bubbling is the boiling point or less of a solvent. The "boiling point of a solvent" refers to a boiling point of either toluene or xylene having a larger % by volume under atmospheric pressure. The boiling point of xylene at one atmospheric pressure is about 140° C. Accordingly, when the chief component of the solvent is xylene, the temperature of $H_2$ bubbling in the case of performing $H_2$ bubbling under one atmospheric pressure is preferably 140° C. or less, more preferably 130° C. or less, and further preferably 120° C. or less. The boiling point of xylene at one atmospheric pressure is about 110° C. Accordingly, when the chief component of the solvent is toluene, the temperature of $H_2$ bubbling in the case of performing $H_2$ bubbling under one atmospheric pressure is preferably 110° C. or less.

3-4-3. Pressure for $H_2$ Bubbling—$H_2$ Partial Pressure $H_2$ bubbling can be carried out under any of ordinary pressure, reduced pressure, and increased pressure, but is preferably carried out under ordinary pressure. The $H_2$ partial pressure of $H_2$ bubbling is between 1 and 30%. This is because a lower $H_2$ partial pressure may not sufficiently reduce palladium, and a higher $H_2$ partial pressure may rapidly reduce palladium to be aggregated. The lower limit of the $H_2$ partial pressure is preferably 2%, 3%, 4%, or 5%. This is because the catalytic activity of a zeolite-palladium complex is particularly elevated in such a case. The upper limit of the $H_2$ partial pressure is 25%, 20%, 15%, 10%, or 7%. This is because palladium readily forms an atomic state or a microcluster of palladium having a coordination number of 4 or less. A component other than hydrogen preferably employs inert gas, and, for example, nitrogen or argon.

3-4-4. Duration of $H_2$ Bubbling

The duration of $H_2$ bubbling is not particularly limited, but the $H_2$ bubbling may be carried out for a time sufficient to reduce palladium. The duration of $H_2$ bubbling is, for example, 5 minutes or more, and preferably 30 minutes or more. For example, the upper limit of $H_2$ bubbling is, but is not limited to, 1, 2, 5, 10, or 20 hours. Provided that $H_2$ bubbling is carried out during which a zeolite-palladium complex catalyzes a chemical reaction, the catalytic activity of the zeolite-palladium complex is markedly enhanced. Accordingly, in this case, it is preferable to continue $H_2$ bubbling until the chemical reaction is completed.

4. Method for Producing Suzuki-Miyaura Coupling Compound 4-1. First Embodiment

A method for producing a Suzuki-Miyaura coupling compound of the first embodiment of the present invention includes the step of carrying out a coupling reaction of reactants of a Suzuki-Miyaura coupling reaction in a solvent containing at least one of xylene and toluene under the presence of a zeolite-palladium complex as illustrated in the above section "1. Zeolite-Palladium Complex" or as produced by a method illustrated in the above section "3. Method for Producing Zeolite-Palladium Complex". As described above, a zeolite-palladium complex of this embodiment possesses very high catalytic activity for a Suzuki-Miyaura coupling reaction. Accordingly, the Suzuki-Miyaura coupling compound can be highly efficiently produced.

4-1-1. Suzuki-Miyaura Coupling Reaction

According to a Suzuki-Miyaura coupling reaction, $R^1B(OR^2)_2$ or $(R^1)_3B$ (wherein $R^1$ represents aryl, vinyl, or alkyl; and $R^2$ represents hydrogen or alkyl) can react with $R^3X$ (wherein $R^3$ represents aryl or vinyl; and X represents halogen or triflate($(OTf)_3$)) to yield a biaryl compound, an alkylaryl compound, an alkenylaryl compound or a diene compound. Examples of the aryl typically include those having a carbon number of 6 to 10 and preferably those having a carbon number of 6 such as, for example, phenyl and naphthyl. In addition, this vinyl may optionally have a substituent. The halogen is chlorine, bromine, or iodine, and is preferably iodine or bromine.

The reaction temperature of this reaction is between 70° C. and 150° C., and preferably around 100° C. The reaction time depends on its substrate. However, the reaction is terminated at 1 hour to 24 hours, and usually within several hours.

4-1-2. Solvent

The above coupling reaction is made to be performed in a solvent containing at least one of xylene and toluene. The description of this solvent has been precisely described in the above "3-4-1. Solvent for $H_2$ Bubbling".

4-1-3. $H_2$ Bubbling

During the above coupling reaction, $H_2$ bubbling is preferably carried out at a temperature between 20° C. and 170° C. under an $H_2$ partial pressure of 1 to 30%. This is because even without $H_2$ bubbling, the coupling reaction is promoted by an action of the catalyst, and with $H_2$ bubbling, the reaction further efficiently proceeds. The suitable solvent, temperature, $H_2$ partial pressure, and duration of the $H_2$ bubbling is precisely described in the sections 3-4-1 to 3-4-4.

4-1-4. Posttreatment after Reaction

As to posttreatment after the reaction, a zeolite-palladium complex can be removed and collected by filtration, and a target substance can be obtained by extraction, concentration, and purification of the filtrate. Usually, there is no leak of palladium from the reaction and posttreatment operation.

4-2. Second Embodiment

A method for producing a Suzuki-Miyaura coupling compound of the second embodiment of the present invention includes the steps of producing a zeolite-palladium complex by carrying out $H_2$ bubbling over a zeolite-palladium complex precursor as obtained by mixing $NH_4^+$-containing USY-zeolite with a palladium ammonium salt, in a solvent containing at least one of xylene and toluene at a temperature between 20° C. and 170° C. under an $H_2$ partial pressure of 1 to 30% in the presence of reactants of a Suzuki-Miyaura coupling reaction; and simultaneously subjecting the reactants to the coupling reaction.

In the first embodiment, a zeolite-palladium complex in which palladium has already been reduced by $H_2$ bubbling is used to produce a coupling compound. In contrast, in this embodiment, a zeolite-palladium complex precursor prior to reduction of palladium is used to produce a coupling compound. In this embodiment, $H_2$ bubbling is carried out in the presence of a zeolite-palladium complex precursor and reactants of a coupling reaction, so that this precursor is reduced to form a zeolite-palladium complex having catalytic activity and simultaneously the coupling reaction is promoted by a catalytic action of this complex. This embodiment achieves an advantage of saving operations of performing beforehand $H_2$ bubbling over the precursor.

The zeolite-palladium complex precursor has been precisely described in the section "3-3. Precursor of Zeolite-Palladium Complex". The $H_2$ bubbling has been precisely described in the section "3-4. $H_2$ Bubbling".

EXAMPLES

In Examples 1 to 8, a commercially available $NH_4$—USY-zeolite was subjected to calcination to prepare $NH_4$-containing USY-zeolite, which was used to prepare a zeolite-palladium complex precursor. After Example 9, in order to optimize the physicality of $NH_4$-contining USY-zeolite, the present inventors by themselves carried out steaming treatment for commercially available $NH_4$—Y-zeolite under various conditions to prepare H—USY-zeolite. Then, $NH_4$-containing USY-zeolite was used which was prepared by ion exchange of this H—USY-zeolite with an ammonium salt, followed by calcination.

Remarkably, when the $NH_4$-containing USY-zeolite as prepared by the present inventors by themselves was used, the catalytic performance of the zeolite-palladium complex increased two times or more. Hereinafter, the respective Examples are illustrated in detail.

Example 1

Effect of $H_2$ Bubbling on Catalytic Activity

In Example 1, $NH_4$—USY-zeolite was subjected to calcination, and $NH_4$-containing USY-zeolite in which $NH_4^+$ had been partially left was prepared. Then, this zeolite and tetraammine palladium chloride were mixed and stirred to prepare a zeolite-palladium complex precursor. For this precursor, the catalytic activity was examined in the cases of: (1) no $H_2$ bubbling; (2) $H_2$ bubbling only during a Suzuki-Miyaura coupling reaction; (3) $H_2$ bubbling only before a Suzuki-Miyaura coupling reaction; and (4) $H_2$ bubbling both before and during a Suzuki-Miyaura coupling reaction. The catalytic activity was higher in the case of carrying out $H_2$ bubbling before or during the reaction than in the case of no $H_2$ bubbling. The catalytic activity was found to be the highest in the case of carrying out $H_2$ bubbling both before and during the reaction.

Hereinafter, the details of the experiments are described.
1. Method for Preparing Catalyst
1-1. Preparation of TAPd Solution To 250-ml measuring flask was added 0.6189 g of tetraammine palladium chloride monohydrate (manufactured by Sigma-Aldrich Corporation), and deionized water was further added until reaching a marked line (Pd-0.001 g/ml). The resulting solution is referred to as the "TAPd solution".
1-2. Preparation of Zeolite-Palladium Complex Precursor (the Supported Amount of Pd: 0.4 wt %)

According to the following method, a zeolite-palladium complex precursor as used in this Example was prepared.

1) $NH_4$—USY (manufactured by Tosoh Corporation, HSZ-341NHA $SiO_2/Al_2O_3$=7.7) was subjected to calcination under an $N_2$ atmosphere at 500° C. for 4 hours. This calcination was carried out by flowing nitrogen from one end of a glass tube under conditions in which $NH_4$—USY had been packed in the glass tube. In this method, the nitrogen flow was not sufficient, so that $NH_3$ generated did not readily flow out from the glass tube. As a result, $NH_4^+$ did not completely detach and $NH_4$-containing USY was yielded. As determined by a temperature-programmed desorption method (TPD), the $NH_4^+$ content was about 0.2 mol/kg.

2) Next, 300 ml of deionized water, 12 ml of the TAPd solution, and 3 g of $NH_4$-containing USY as prepared in the above 1) were weighed and added to a 500-ml Erlenmeyer flask.

3) After stirred at room temperature for 12 hours, the mixture was subjected to ion exchange.

4) Suction filtration and washing were performed, and a solid left on a filter paper was then dried in a dryer at 50° C. for 8 hours. This procedure yielded a zeolite-palladium complex precursor in which Pd had not been reduced.
1-3. Method for $H_2$ Bubbling before Coupling Reaction (Pretreatment)

A tube for flowing 6% $H_2$ diluted with Ar was connected to a reaction apparatus as shown in FIG. 1, and a solvent (o-xylene) and the above precursor were subjected to bubbling at room temperature for 30 minutes while stirring. At this occasion, a stirrer was made to be vigorously stirred, so that the catalyst was completely reduced. The $H_2$ flow rate was set to 30 ml/min.
2. Reaction Procedure
2-1. Conditions for Suzuki-Miyaura Coupling Reaction For a Suzuki-Miyaura coupling reaction, 1.0 mg of the catalyst, 100 mmol of bromobenzene, 160 mmol of phenylboronic acid, 200 mmol of potassium carbonate, 280 ml of o-xylene, and tridecane (internal standard material) were added to a three-neck flask. Then, a reaction was carried out under an $N_2$ atmosphere in an oil bath at a temperature of 110° C. while stirring.
2-2. Analysis of Reaction—Reaction Conditions For both reactions, a small amount of a postreaction solution in the respective time course was collected, diluted with acetone, and analyzed with a capillary gas chromatography device equipped with an FID detector (Shimadzu GC-2010).

Figure 2:
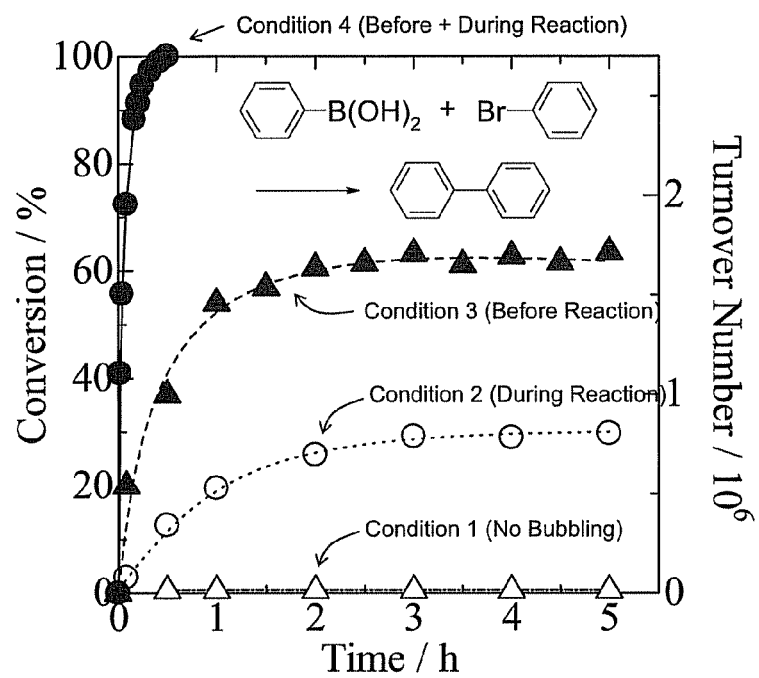
FIG. 2 is a graph showing an effect of H$_2$ bubbling according to Example 1.

In addition, in order to investigate an effect of $H_2$ flow during the reaction on the catalytic activity, a tube for flowing 6% $H_2$ diluted with Ar was inserted in a reaction solution depending on the need, and $H_2$ bubbling was carried out. The $H_2$ flow rate was set to 30 ml/min.
3. Experimental Results FIG. 2 shows time course changes of the conversion rate of bromobenzene to biphenyl by a Pd/H—USY catalyst during a Suzuki-Miyaura coupling reaction. When $H_2$ bubbling over the reaction solution was carried out during the reaction under the presence of the catalyst which had been subjected to pretreatment by $H_2$ bubbling, the catalytic activity was markedly elevated. Then, the conversion rate reached 100%, and the reaction was completed at 30 minutes (see the symbol "●" in the plot of FIG. 2). In addition, the TON of Pd at completion of the reaction was 2,700,000 which was remarkably high. Also, biphenyl was yielded quantitatively, and a byproduct was not generated. Such catalytic activity was demonstrated to be markedly high compared to the case without performing $H_2$ bubbling during the reaction under the presence of the catalyst which had been subjected to the pretreatment (see the symbol "▲" in the plot of FIG. 2). In contrast, in the case of performing $H_2$ bubbling during the reaction without performing pretreatment of the catalyst by $H_2$ bubbling, the catalytic activity was lower than that of the case of performing $H_2$ bubbling only in the pretreatment (see the symbol "○" in the plot of FIG. 2). In the case without performing $H_2$ bubbling, there was almost no activity (see the symbol "□" in the plot of FIG. 2).

Example 2

Effect of Kind of Pd Salt

In Example 2, a Pd salt to prepare a precursor was variously changed. A Suzuki-Miyaura coupling reaction was carried out under the same condition as Example 1 except this change. $H_2$ bubbling was performed only before the reaction. Table 1 shows the results.

As clearly demonstrated by referring to Table 1, when a tetraammine palladium salt was used, the catalytic activity was found to be markedly higher than that of the cases using other salts.

TABLE 1

| Entry | Precursor | Pd/ $10^{-4}$ mol % | Time/h | Yield/% | TON |
|---|---|---|---|---|---|
| 1[b] | $Pd(NH_3)_4Cl_2$ | 0.4 | 2.0 | 64 | 1,700,000 |
| 2[b] | $Pd(NH_3)_4(NO_3)_2$ | 0.4 | 2.0 | 64 | 1,700,000 |
| 3[c] | $Pd(OAc)_2$ | 0.7 | 3.0 | 25 | 340,000 |
| 4[c] | $PdCl_2$ | 0.7 | 3.0 | 0 | 0 |

Example 3

Dependency on Reactants of Coupling Reaction

In Example 3, reactants of a coupling reaction were variously changed. A Suzuki-Miyaura coupling reaction was carried out under the same condition as Example 1 except the following conditions.

1. Conditions for Suzuki-Miyaura Coupling Reaction

For a reaction, 1.0 mg (Pd: $3.8 \times 10^{-8}$ mol) of the catalyst, 200 mmol of aryl bromide, 320 mmol of phenylboronic acid, 400 mmol of potassium carbonate, 520 ml of o-xylene, and tridecane (internal standard material) were added to a three-neck flask. Then, the reaction was carried out under an $N_2$ atmosphere in an oil bath at a temperature of 110° C. while stirring. In addition, the amount of the catalyst was kept constant, but the scale was modified to carry out the reaction. $H_2$ bubbling was carried out at 110° C. both before and during the reaction.

2. Experimental Results

Table 2 shows the experimental results. By referring to the Turnover Number (TON) in Table 2, when a bromobenzene derivative was used, the TON became very large. When 4-chloroacetophenone was used, the TON was found to become relatively small. However, even if 4-chloroacetophenone was used, it was revealed that appropriate selection of the reaction conditions allowed the yield to remarkably increase.

TABLE 2

Results of Suzuki-Miyaura reaction catalyzed by 0.4 wt %-Pd/USY[a]
Ar—Br, Ar—Cl + Ph—B(OH)$_2$ → Ar—Ph.

| Entry | Ar—Br, Cl | Pd conc./ mol %[e] | Yield/% | Time/h | Turnover Number |
|---|---|---|---|---|---|
| 1[b] | $C_6H_5Br$ | $1.7 \times 10^{-5}$ | 89 | 3 | 5,300,000 |
| 2[c] | $C_6H_5Br$ | $6.6 \times 10^{-5}$ | 67 | 3 | 1,000,000 |
| 3[b] | $4-NH_2C_6H_4Br$ | $7.8 \times 10^{-5}$ | 86 | 8 | 1,100,000 |
| 4[b] | $4-CHOC_6H_4Br$ | $3.3 \times 10^{-5}$ | 99 | 0.5 | 3,000,000 |
| 5[b] | $4-CH_3C_6H_4Br$ | $2.5 \times 10^{-5}$ | 99 | 1 | 4,000,000 |
| 6[b] | $4-CH_3OC_6H_4Br$ | $1.7 \times 10^{-5}$ | 99 | 4 | 6,000,000 |
| 7[b] | $4-CH_3COC_6H_4Br$ | $0.9 \times 10^{-5}$ | 99 | 1.5 | 11,000,000 |
| 8[b] | $4-CH_3COC_6H_4Cl$ | $7.5 \times 10^{-2}$ | 3 | 3 | 40 |
| 9[d] | $4-CH_3COC_6H_4Cl$ | $7.5 \times 10^{-2}$ | 92 | 1 | 1,300 |

[a]The scales of all reagents were changed, while the catalyst weight was fixed at 1.0 mg.
[b]Reaction was carried out in o-xylene under 6%-$H_2$ bubbling.
[c]Reaction was carried out in o-xylene in an atmosphere of 6% $H_2$.
[d]Reaction condition: ArCl (2.5 mmol), Ph—B(OH)2 (4 mmol), catalyst (50 mg), Cs2CO3 (5 mmol), DMF (6 mL), $H_2O$ (0.1 ml), 383 K, Ar atmosphere.
[e]Mol % with respect to the bromobenzene derivatives.

Example 4

Analysis of Oxidation State and Dispersion State of Pd

Figure 3:
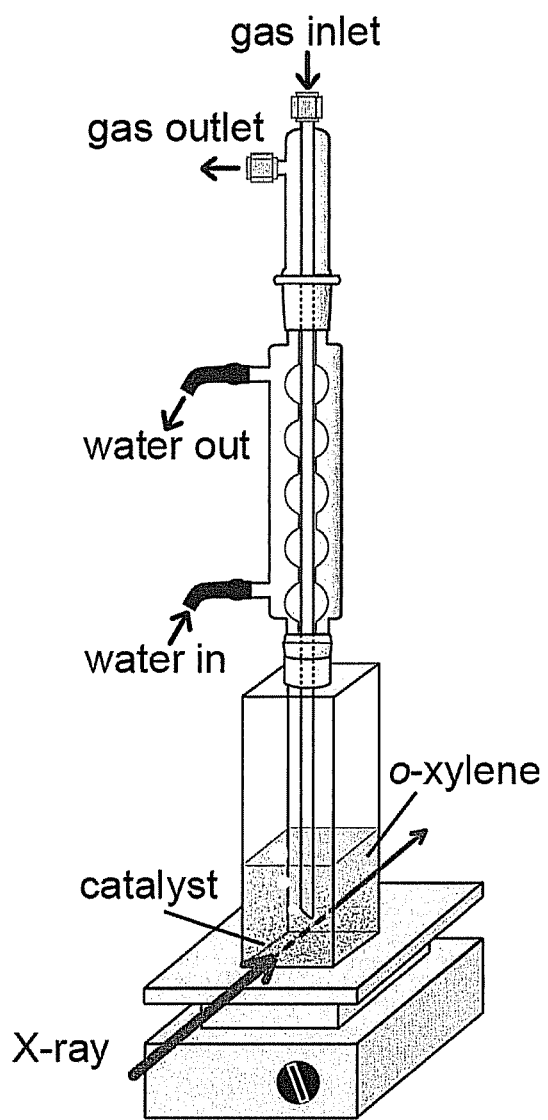
FIG. 3 shows an apparatus for performing the XANES or EXAFS measurement during H$_2$ bubbling.

In Example 4, $H_2$ bubbling over a zeolite-palladium complex precursor as prepared under the same condition as Example 1 was carried out in o-xylene by using an apparatus shown in FIG. 3. Then, XANES and EXAFS were determined at room temperature. For the measurements, SPring-8 BL01B1 was employed.

1. Results of XANES Measurements

Figure 4:
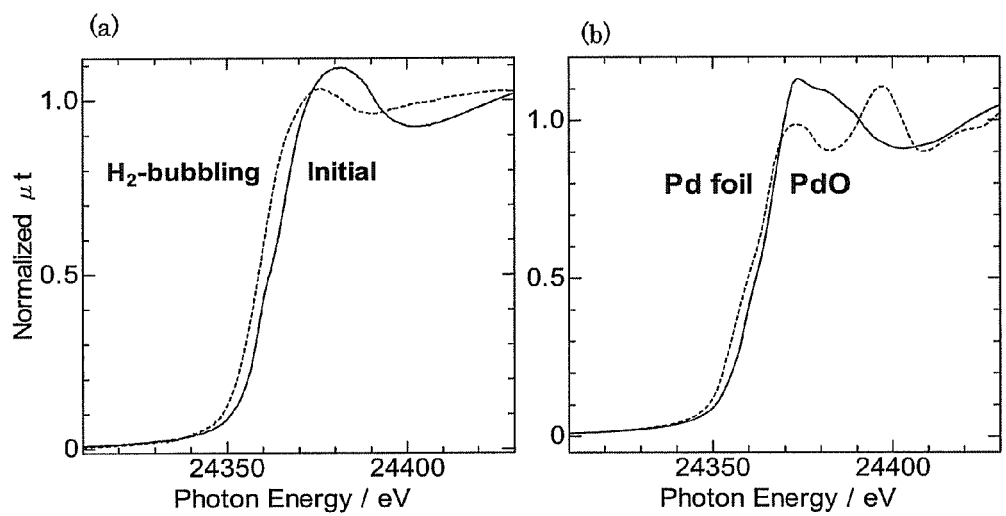
FIG. 4 shows spectra as obtained by the XANES measurement according to Example 4.

FIG. 4 shows the results of XANES measurements. FIG. 4(a) shows XANES spectra at the Pd K-absorption edge of PD/USY before and after 6% $H_2$ bubbling (in o-xylene at 110° C.). FIG. 4(b) shows XANES spectra at the Pd K-absorption edge of a reference sample. When FIG. 4(a) is referred to, $H_2$ bubbling is found to cause the absorption edge of the spectra to shift to a lower energy side. The position of the absorption edge after the shift almost corresponds to that of Pd foil (i.e., the oxidation number is 0) as shown in FIG. 4(b). This results demonstrated that $H_2$ bubbling in o-xylene at 110° C. caused Pd to be reduced.

2. Results of EXAFS Measurements

Figure 5:
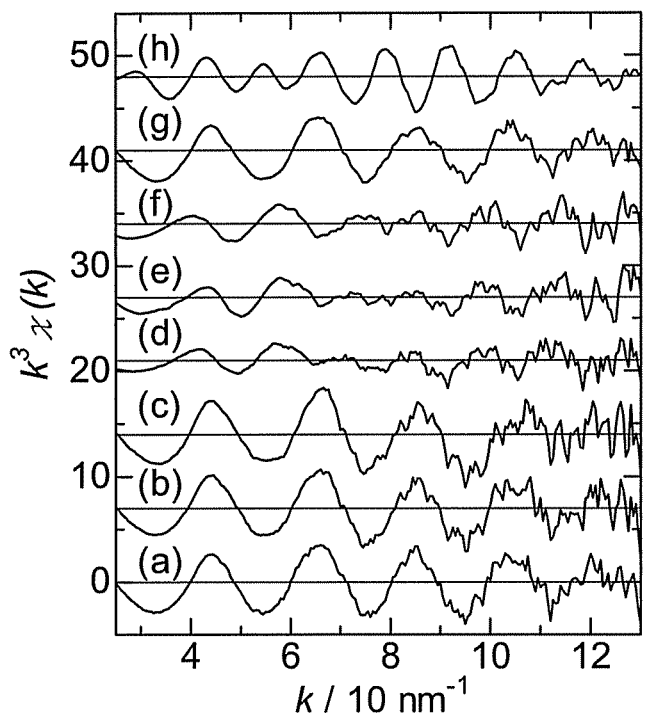
FIG. 5 shows EXAFS spectra at Pd K-absorption edge at various reaction temperatures according to Example 4.
Figure 6:
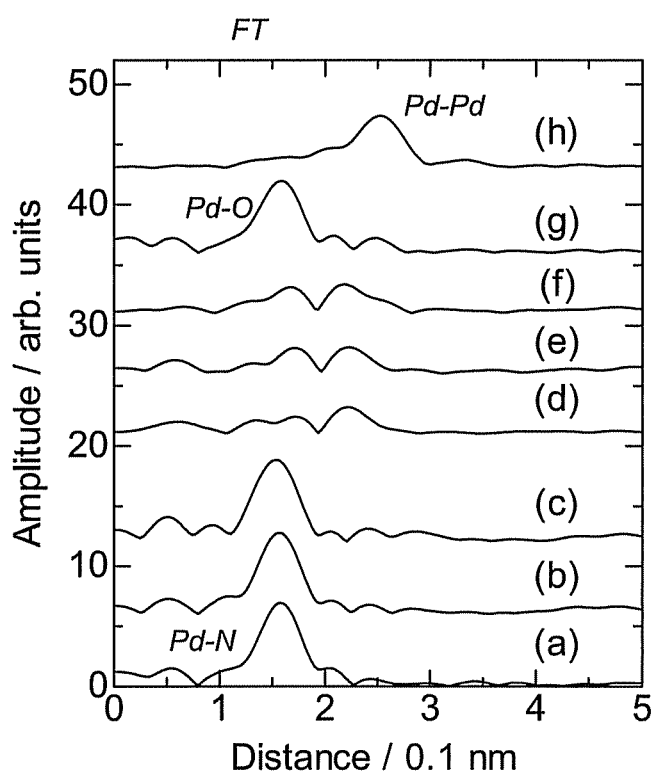
FIG. 6 shows spectra as obtained by Fourier transforms of the spectra of FIG. 5.

FIGS. 5 and 6 show the results of EXAFS measurements. FIG. 5 shows EXAFS spectra at PD K-absorption edge under various reaction temperatures. FIG. 6 shows Fourier transforms of these spectra. The (a) to (h) of FIGS. 5 and 6 correspond to the conditions as shown in Table 3. Fourier transforms were conducted within a range between 25 and 130 $nm^{-1}$ by extracting vibrations by a cubic spline method.

TABLE 3

| | |
|---|---|
| a | No $H_2$ bubbling (Zeolite-Palladium complex precursor) |
| b | 6%-$H_2$ bubbling at 50° C. |
| c | 6%-$H_2$ bubbling at 80° C. |
| d | 6%-$H_2$ bubbling at 100° C. |
| e | 6%-$H_2$ bubbling at 110° C. |
| f | Exposing (e) to the air under room temperature |
| g | After removal of o-xylene, exposing (e) to the air under room temperature |
| h | Exposing a zeolite-palladium complex precursor to 6% $H_2$ without a solvent at room temperature |

Next, as to the spectra of (a), (e), and (h), the spectra which had been inverse Fourier transformed into k-space within a range between 0.11 and 0.32 nm were analyzed within a range between 25 and 130 nm$^{-1}$ by a curve-fitting method. For the structural analysis, PdO, CdS, and Pd foil were used as standard samples for PD—O, Pd—Al, and Pd—Pd, respectively. The analysis used Rex2000 (ver. 2.5) developed by Rigaku, Inc. Table 4 shows the analysis results obtained.

TABLE 4

Curve-fitting analysis of Pd K-edge EXAFS data Pd/USY[a]

| Treatment | Scatter | CN[b] | R/0.1 nm[c] | $\Delta E_0$/eV[d] | DW/0.1 nm[e] | $R_f$/%[f] |
|---|---|---|---|---|---|---|
| Initial | N | 3.6 | 2.02 | −2 | 0.067 | 0.1 |
| 6%-H$_2$ bubbling at 383 K | O(zeolite) | 1.3 | 2.16 | 2 | 0.074 | 0.7 |
| | Al(zeolite) | 1.0 | 2.61 | 14 | 0.044 | |
| 6%-H$_2$ exposure at 300 K | Pd | 6.1 | 2.74 | 0 | 0.09 | 0.4 |
| Pd foil[g] | Pd | (12) | (2.74) | | | |
| PdO[g] | O | (4) | (2.02) | | | |
| | Pd | (4) | (3.14) | | | |
| | Pd | (8) | (3.42) | | | |

[a]Fourier transform range: 25-130 nm$^{-1}$, Fourier filtering range: 0.11-0.32 nm.
[b]Coordination number (error is estimated to be 20%).
[c]Bond distance (±0.001 nm).
[d]Difference in the origin of photoelectron energy between the reference and the sample.
[e]Debye-Waller factor.
[f]Residual factor.
[g]Data from X-ray crystallography.

When Table 4 was referred to, a Pd—N peak was observed in (a) in which H$_2$ bubbling was not carried out. This indicates that Pd is not reduced. For (e) in which H$_2$ bubbling was carried out at 383 K (110° C.), Pd—and Pd—Al peaks were observed, but no Pd—Pd peak was observed. This indicates that Pd becomes an atomic state on the zeolite. In addition, for (h) in which Pd was exposed to hydrogen gas without a solvent at room temperature, many Pd—Pd peaks were observed. This indicates that Pd becomes a large cluster state.

In view of the above, it was verified that when H$_2$ bubbling was carried out at 383 K (110° C.) in o-xylene, Pd became an atomic state and dispersed.

Example 5

Effect of H$_2$ Partial Pressure on H$_2$ Bubbling

In Example 5, the dispersion state and catalytic activity of Pd were investigated when H$_2$ bubbling was carried out under various H$_2$ partial pressures in o-xylene at 383 K (110° C.) for for a zeolite-palladium complex precursor as prepared under the same condition as Example 1.

1. Dispersion State of Pd

Figure 7:
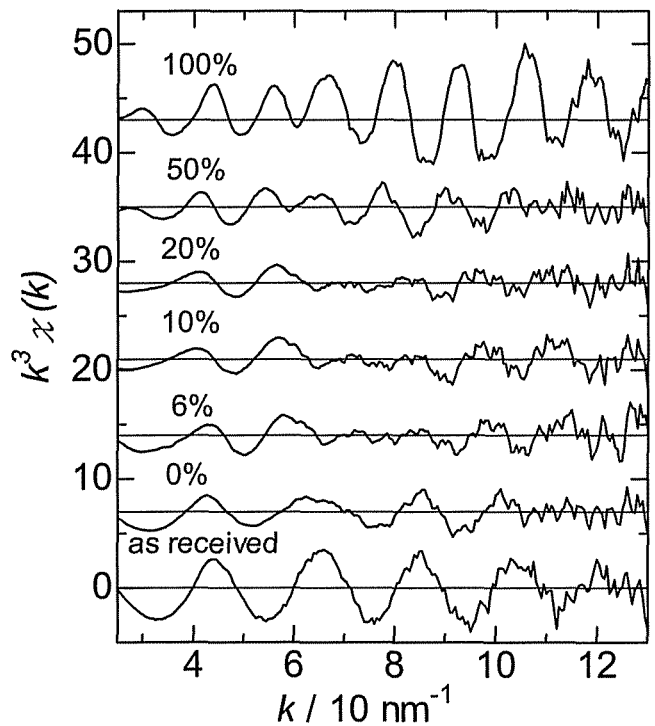
FIG. 7 shows EXAFS spectra at Pd K-absorption edge under the respective $H_2$ partial pressures according to Example 5.
Figure 8:
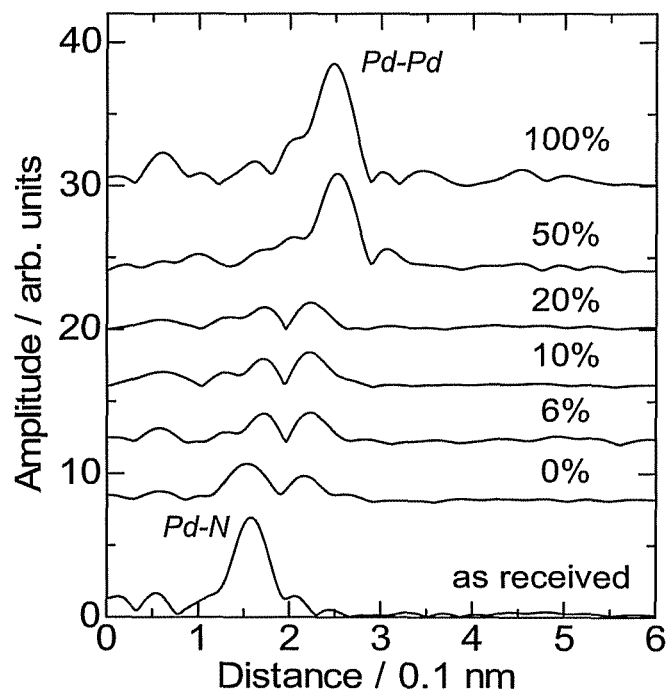
FIG. 8 shows spectra as obtained by Fourier transforms of the spectra of FIG. 7.

By a method similar to Example 4, EXAFS was determined, and the resulting spectra were subjected to Fourier transforms. FIGS. 7 and 8 show the results of EXAFS measurements. FIG. 7 shows EXAFS spectra at Pd K-absorption edge under the respective H$_2$ partial pressures. FIG. 8 shows Fourier transforms of these spectra. When FIG. 8 is referred to, the following is revealed. Since a very large peak is recognized for the cases having an H$_2$ partial pressure between 50 and 100%, aggregation of Pd seems to occur. In addition, for the case having an H$_2$ partial pressure of 0, a Pd—N peak is recognized. Thus, reduction of Pd$^{2+}$ itself does not occur. For the cases having an H$_2$ partial pressure between 6 and 20%, no Pd—Pd peak is observed. Accordingly, Pd becomes an atomic state.

2. Catalytic Activity

Figure 9:
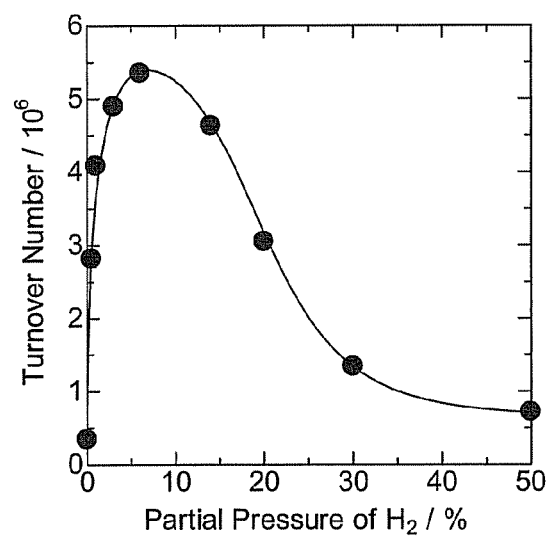
FIG. 9 is a graph indicating a relationship between an $H_2$ partial pressure and a TON according to Example 5.

A Suzuki-Miyaura coupling reaction of bromobenzene with phenylboronic acid was carried out under the same condition as Example 3 except the point in which the H$_2$ partial pressure was altered. FIG. 9 shows the results.

When FIG. 9 was referred to, in the cases having an H$_2$ partial pressure between 1 and 30%, the catalytic activity was markedly high. In the case having an H$_2$ partial pressure of 6%, the maximal catalytic activity was found to be achieved.

Example 6

Effect of Solvent

In Example 6, the dispersion state and catalytic activity of Pd were investigated when H$_2$ bubbling was carried out in various solvents at between 373 K (100° C.) and 383 K (110° C.) over a zeolite-palladium complex precursor as prepared under the same condition as Example 1.

1. Dispersion State of Pd

Figure 10:
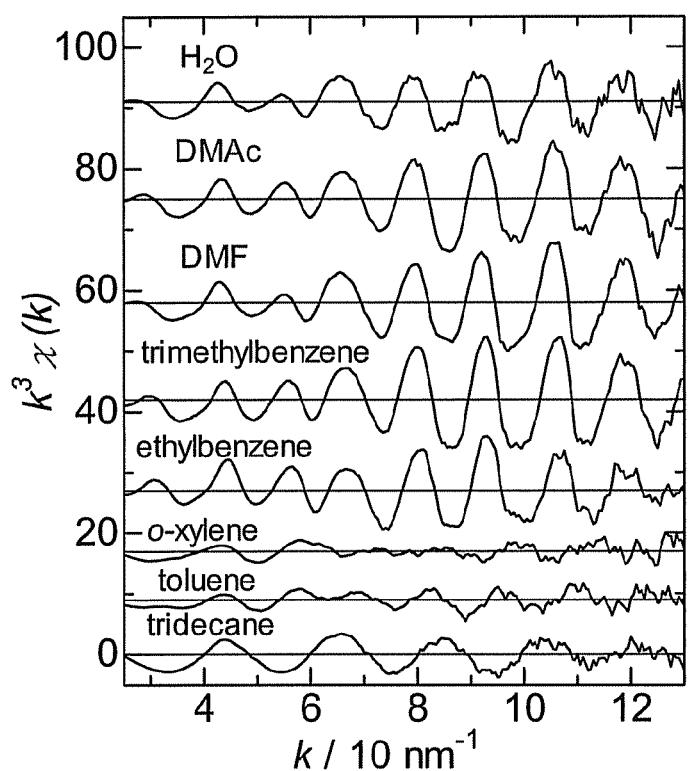
FIG. 10 shows EXAFS spectra at Pd K-absorption edge in various solvents according to Example 6.
Figure 11:
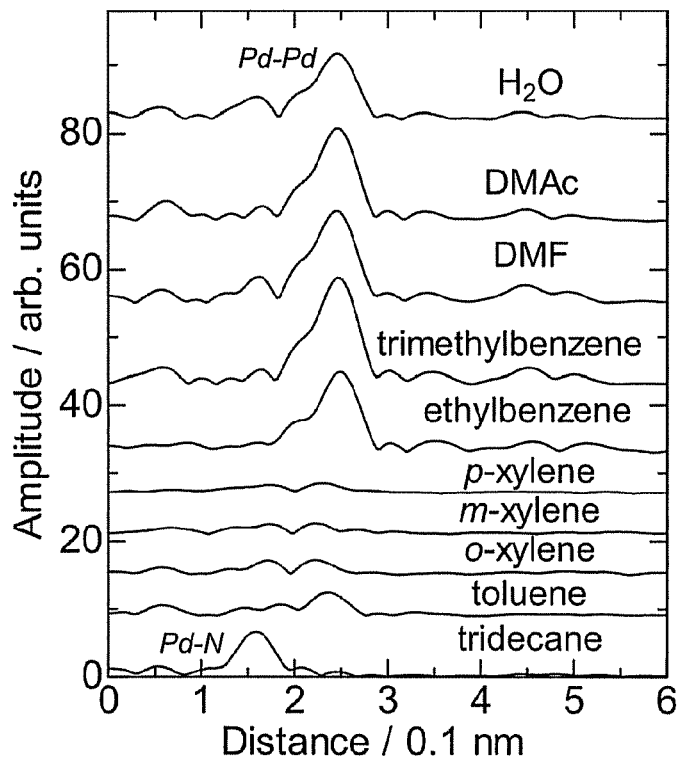
FIG. 11 shows spectra as obtained by Fourier transforms of the spectra of FIG. 10.

By a method similar to Example 4, EXAFS was determined, and the resulting spectra were subjected to Fourier transforms. FIGS. 10 and 11 show the results of EXAFS measurements. FIG. 10 shows EXAFS spectra at Pd K-absorption edge in various solvents. FIG. 11 shows Fourier transforms of these spectra.

When FIG. 11 is referred to, the following is understood. For water, DMAc, DMF, 1,3,5-trimethylbenzene, and ethylbenzene, a very large Pd—Pd peak is recognized. Accordingly, aggregation of PD seems to occur. For tridecane, a Pd—N peak is recognized. Thus, reduction of Pd$^{2+}$ itself does not seem to occur. Actually, H$_2$ bubbling in tridecane failed to cause the catalyst to turn black which was evidence of generation of metallic palladium, and the color remained white. For toluene, a Pd—Pd micropeak was observed. When analyzed in a manner similar to Example 3, the Pd—Pd coordination number was found to be 2.1. This number means that about three atoms of Pd form a microcluster. For o-xylene, no Pd—Pd peak was observed. Thus, Pd was found to become an atomic state. In addition, for m- and p-xylene. Pd was found to become an atomic state in a manner similar to o-xylene.

2. Catalytic Activity

A Suzuki-Miyaura coupling reaction of bromobenzene with phenylboronic acid was carried out under the same condition as Example 3 except the point in which the solvent was altered. Table 5 shows the results.

When the Turnover Number (TON) shown in Table 5 was referred to, in the case of using o-xylene, the catalytic activity was remarkably high. In the case of using toluene, the second highest catalytic activity was achieved. In the cases of using solvents other than those, the catalytic activity was not high. As described above, in o-xylene. Pd was an atomic state and dispersed. In toluene, Pd dispersed in a microcluster state having about three atoms of Pd. In a solvent other than those, Pd aggregated. The above revealed that the dispersion state and catalytic activity of Pd correlated.

TABLE 5

Results of Suzuki-Miyaura reactions between bromobenzene and phenylboronic acid catalyzed by 0.4 wt %-Pd/USY[a]

| Entry | Solvent | Pd conc./ mol %[b] | Temp./ K | Yield/% | Turnover Number |
|---|---|---|---|---|---|
| 1 | H$_2$O | 7.5 × 10$^{-4}$ | 373 | 8 | 12,000 |
| 2 | DMAc | 7.5 × 10$^{-4}$ | 383 | 11 | 17,000 |
| 3 | DMF | 7.5 × 10$^{-4}$ | 383 | 22 | 36,000 |

TABLE 5-continued

Results of Suzuki-Miyaura reactions between bromobenzene and phenylboronic acid catalyzed by 0.4 wt %-Pd/USY[a]

| Entry | Solvent | Pd conc./ mol %[b] | Temp./ K | Yield/% | Turnover Number |
|---|---|---|---|---|---|
| 4 | 1,3,5-trimethylbenzene | $7.5 \times 10^{-4}$ | 383 | 32 | 49,000 |
| 5 | ethylbenzene | $7.5 \times 10^{-4}$ | 383 | 12 | 19,000 |
| 6 | o-xylene | $1.7 \times 10^{-5}$ | 383 | 89 | 5,300,000 |
| 7 | toluene | $7.5 \times 10^{-4}$ | 383 | 59 | 89,000 |
| 8 | tridecane | $7.5 \times 10^{-4}$ | 383 | 5 | 8,000 |

[a]The scales of all reagents were changed, while the catalyst weight was fixed at 1.0 mg. Reaction time, 3 h.
[b]Mol % with respect to bromobenzene.

Example 7

Effect of Calcination Conditions for $NH_4$—USY-zeolite

In Example 7, the dispersion state of Pd, the $NH_4$ content in $NH_4$-containing USY-zeolite as obtained by calcination, and the catalytic activity were investigated when $H_2$ bubbling was carried out over a zeolite-palladium complex precursor as prepared under the same condition as Example 1 under the conditions identical to Example 3 except that the calcination conditions for $NH_4$—USY-zeolite were altered.

1. Dispersion State of Pd

Figure 12:
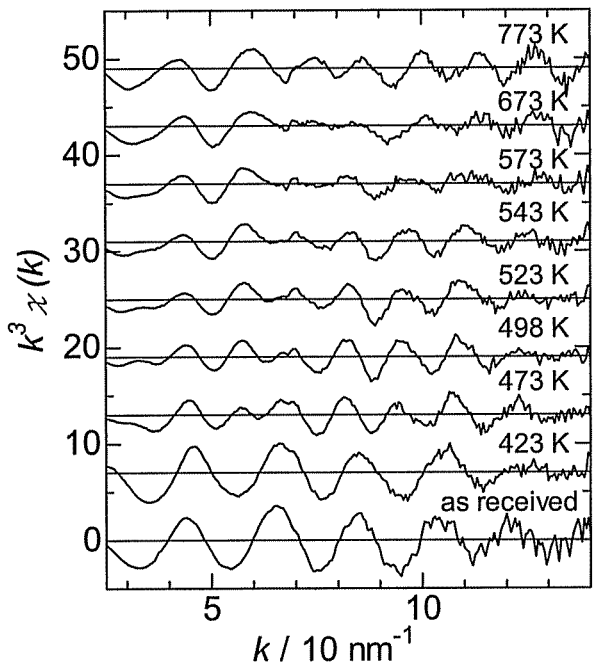
FIG. 12 shows EXAFS spectra at Pd K-absorpton edge when calcination was performed on $NH_4$—USY-zeolite at various temperatures according to Example 7.
Figure 13:
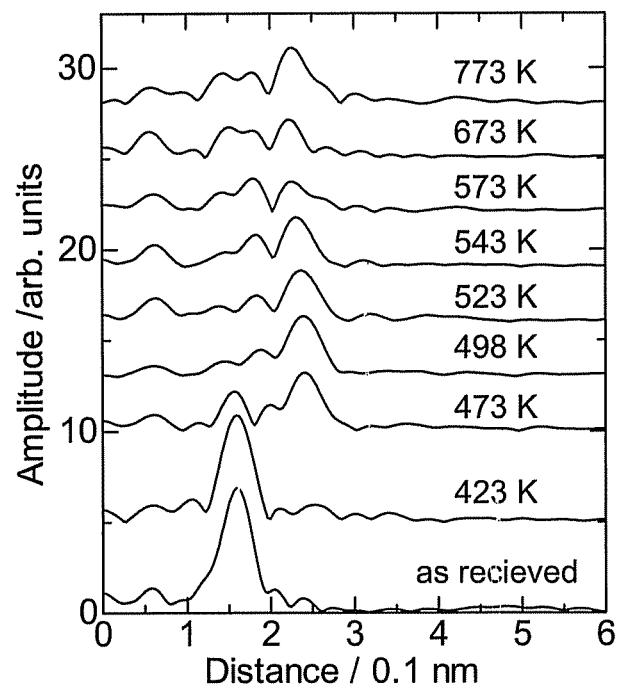
FIG. 13 shows spectra as obtained by Fourier transforms of the spectra of FIG. 12.

By a method similar to Example 4, EXAFS was determined, and the resulting spectra were subjected to Fourier transforms. FIGS. 12 and 13 show the results of EXAFS measurements. FIG. 12 shows EXAFS spectra at Pd K-absorption edge under respective calcination temperatures. FIG. 13 shows Fourier transforms of these spectra. In addition, Table 6 shows the analysis results as obtained by analyzing FIG. 13 by a method similar to Example 4.

When FIG. 13 and Table 6 are referred to, the following is revealed. In the case of calcination at 423 K, Pd is not sufficiently reduced and a bond of Pd—N remains. In the case of calcination at 498 K or 773 K, a small Pd—Pd peak is observed, and Pd becomes a microcluster state. In the case of calcination at 573 K, no Pd—Pd peak is observed, and Pd keeps an atomic state.

TABLE 6

Curve-fitting analysis of Pd K-edge EXAFS data for Pd loaded on USY calcined at different temperatures[a]

| Calcination Temp./K | Scatter | CN[b] | R/0.1 nm[c] | $\Delta E_0$/eV[d] | DW/0.1 nm[e] | $R_f$/%[f] |
|---|---|---|---|---|---|---|
| As-received | N | 3.6 | 2.02 | −2 | 0.067 | 0.1 |
| 423 K | N | 2.6 | 2.02 | 7 | 0.051 | 0.7 |
| 498 K | O(zeolite) | 1.1 | 2.21 | 7 | 0.090 | 0.7 |
|  | Pd | 3.0 | 2.66 | −4 | 0.092 |  |
| 573 K | O(zeolite) | 1.3 | 2.16 | 2 | 0.074 | 0.7 |
|  | Al | 1.0 | 2.61 | 14 | 0.044 |  |
| 773 K | O(zeolite) | 2.1 | 2.25 | 9 | 0.073 | 2.7 |
|  | Pd | 1.0 | 2.57 | 2 | 0.055 |  |

[a]Fourier transform range: 25-130 nm$^{-1}$, Fourier filtering range: 0.17-0.32 nm.
[b]Coordination number (error is estimated to be 20%).
[c]Bond distance (±0.001 nm).
[d]Difference in the origin of photoelectron energy between the reference and the sample.
[e]Debye-Waller factor.
[f]Residual factor.

2. Relationship between Calcination Temperature and $NH_4^+$ Content in Zeolite

The $NH_4^+$ content in $NH_4$-containing USY-zeolite as obtained by calcination was determined by a temperature-programmed desorption method (TPD), and the relationship between the calcination temperature and the $NH_4^+$ content in the zeolite was examined.

The $NH_4^+$ content in the zeolite was measured by a temperature-programmed desorption method (TPD). Specifically, the $NH_4^+$ content in $NH_4$-contining USY-zeolite was determined by measurements of the amount of $NH_3$ detached from the zeolite by heating the $NH_4$-containing USY-zeolite.

Figure 14:
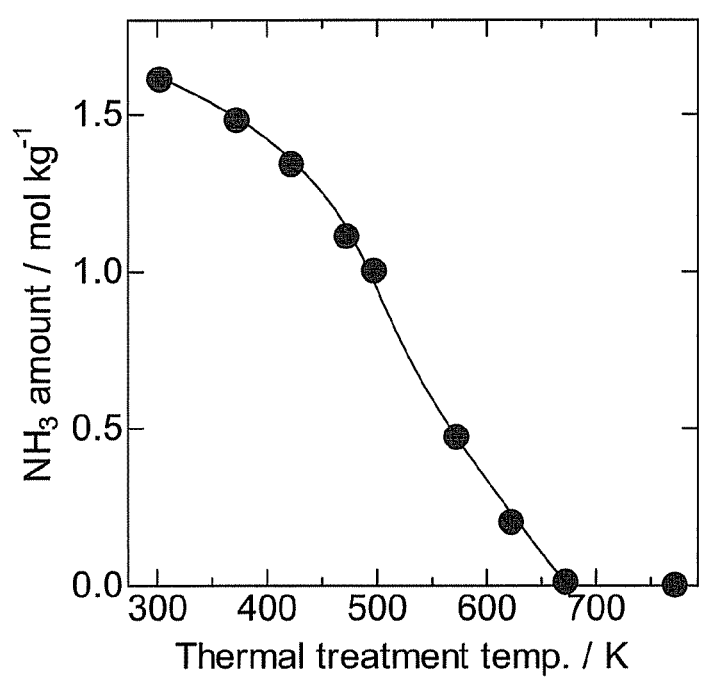
FIG. 14 is a graph indicating a relationship between a calcination temperature of $NH_4$—USY-zeolite and an amount of $NH_3$ according to Example 7.

FIG. 14 shows the results. It was clearly demonstrated by referring to FIG. 14 that as the calcination temperature became higher, the $NH_4^+$ content in the zeolite decreased.

3. Relationship between Calcination Temperature and Catalytic Activity

Figure 15:
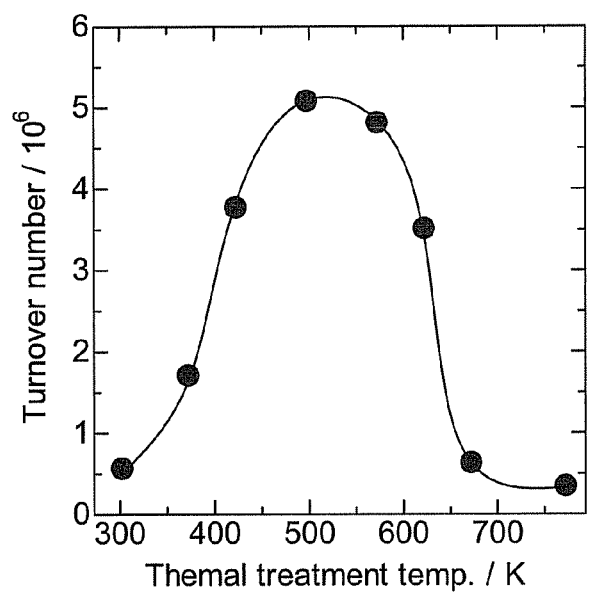
FIG. 15 is a graph indicating a relationship between a calcination temperature of $NH_4$—USY-zeolite and a TON according to Example 7.

A Suzuki-Miyaura coupling reaction of bromobenzene with phenylboronic acid was carried out under the same condition as Example 3 by using a precursor as obtained under the above calcination conditions. FIG. 15 shows the results. As clearly demonstrated by referring to FIG. 15, in the cases of temperatures between 423 K (150° C.) and 623 K (350° C.), the catalytic activity was high, and in the cases of calcination at between 498 K (225° C.) and 573 K (300° C.), the catalytic activity was found to become particularly high. When FIGS. 14 and 15 together are referred to, there is a correlation between the $NH_4^+$ content in the zeolite and the catalytic activity. The $NH_4^+$ contents in the cases of preferable calcination temperatures between 423 K (150° C.) and 623 K (350° C.) are between 0.15 and 1.3 mol/kg. Thus, when the $NH_4^+$ content is between 0.15 and 1.3 mol/kg, the catalytic activity can be said to be elevated.

Example 8

As to Acid Sites in USY Framework

Figure 16:
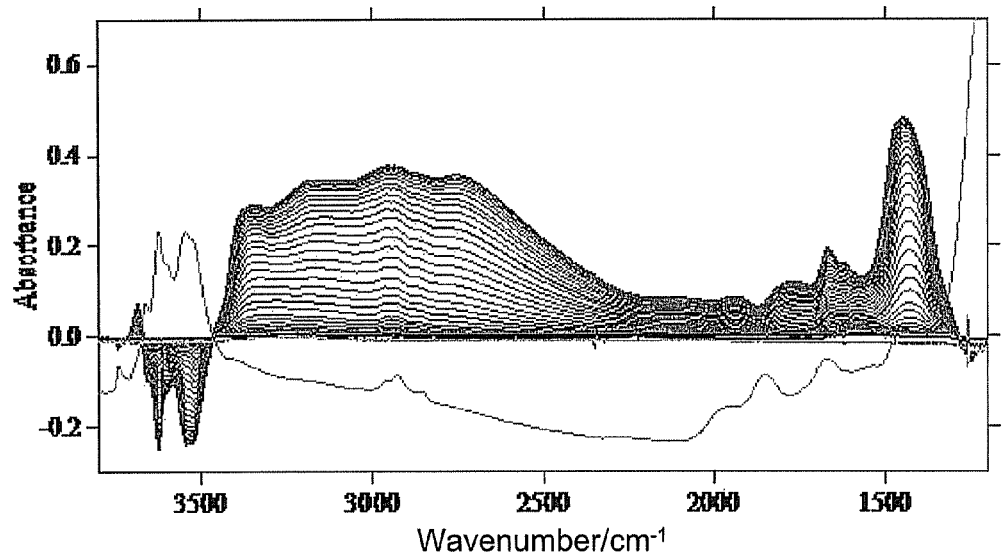
FIG. 16 shows IR difference spectra by IR-TPD of USY-zeolite according to Example 8.
Figure 17:
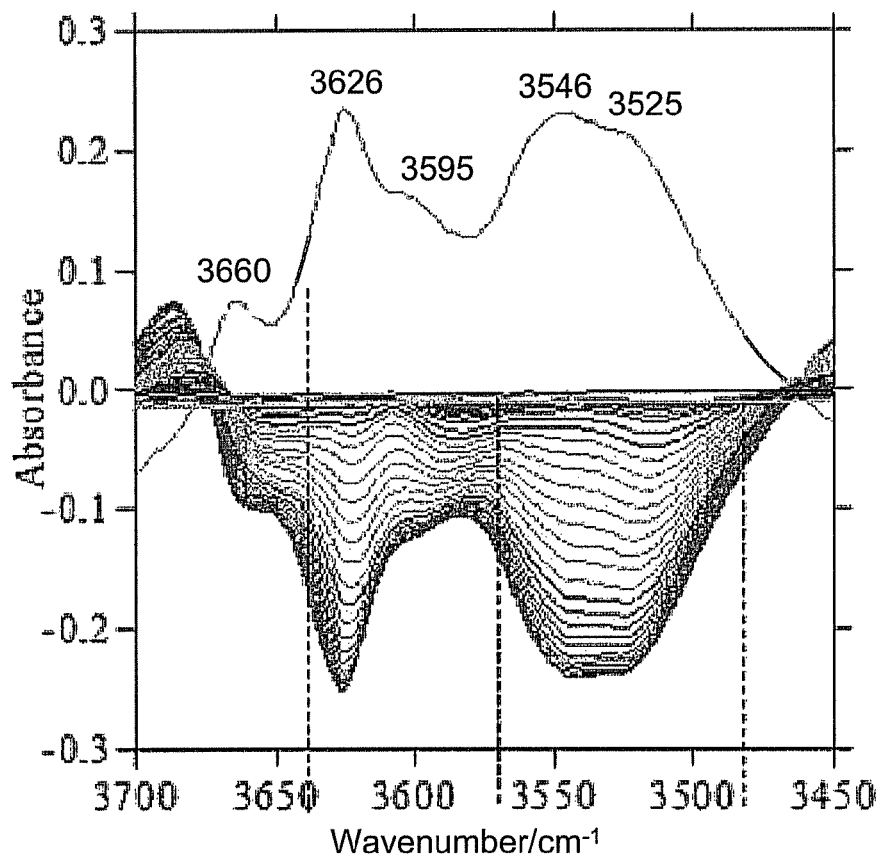
FIG. 17 is a magnified view of the OH bands in FIG. 16.

There exist four acid sites in an USY-zeolite framework. Among them, the present inventors consider that what is called position 3 which exhibits the strongest acid strength among the acid sites and is located or closely located to a Pd atom exerts the activity. As seen in difference spectra by IR-TPD and a magnified view of the OH bands shown in FIGS. 16 and 17, the peak of 3525 cm$^{-1}$ is assigned to the stretching vibration of O3H of a hexagonal prism; the peak of 3546 cm$^{-1}$ is assigned to the stretching vibration of O2H of a sodalite cage; and the peak of 3626 cm$^{-1}$ is assigned to the stretching vibration of O1H of a super cage. In addition, the peak of 3660 cm$^{-1}$ is a peak which is assigned to Al—OH outside the framework. Whereas the peak of 3595 cm$^{-1}$ is considered to be a peak which is usually observed for EDTA-treated USY, this peak was also observed in this USY.

<Discussion>

The acid sites which are observed like this peak of 3595 cm$^{-1}$ seem to contribute to some factors which exhibit high activity for a Suzuki reaction. Since this is closely located to a supercage, a zeolite-palladium complex according to the present invention seems to exhibit high activity.

Example 9

Preparation of Zeolite-Palladium Complex Precursor by Using Self-Produced $NH_4$-Containing USY-Zeolite In Example 9, a zeolite-palladium complex precursor was prepared by using self-produced $NH_4$-containing USY-zeolite. Specifically, the preparation was carried out by the following procedure.

Na—Y-zeolite (manufactured by Tosoh Corporation, NSZ-320NAA) was subjected to ion exchange with $NH_4NO_3$ (0.5 mL/L) three times at 80° C. to yield $NH_4$—Y-zeolite.

Next, the resulting $NH_4$—Y-zeolite was subjected to steaming treatment at 550° C. under a water vapor partial pressure of 18% for 10 hours to yield H—USY-zeolite. The steaming treatment was carried out: by placing the $NH_4$—Y-zeolite in a quartz tube; by heating water ejected with a microfeeder (syringe) by using a ribbon heater; and by flowing those mixed and diluted with nitrogen at a total flow rate of 50 ml/min.

The resulting H—USY-zeolite was subjected to ion exchange with $NH_4NO_3$ (0.5 mL/L) three times at 80° C. to yield $NH_4$—USY-zeolite.

By carrying out calcination of the resulting $NH_4$—USY-zeolite at 300° C. for 3 hours, $NH_4$ was made to partially detach to yield $NH_4$-containing USY-zeolite. As being different from the method of Example 1, this calcination was carried out in the air under a state in which the $NH_4$—USY-zeolite was made to spread on an evaporating dish.

Next, the resulting $NH_4$-containing USY-zeolite was subjected to ion exchange with a $Pd(NH_3)_4Cl_2$ solution ($3.8 \times 10^{-4}$ mol dm$^{-3}$; Aldrich, St. Louis, Mo., USA) at room temperature. Then, the zeolite was washed with deionized water, and dried overnight at 50° C. to yield a zeolite-palladium complex precursor. According to inductively coupled plasma (ICP) analysis, the supported amount of Pd in this precursor was 0.4 wt %.

Example 10

Effect of $H_2$ Bubbling

In Example 10, effects of $H_2$ bubbling on catalytic activity were examined.

1. Conditions for Suzuki-Miyaura Coupling Reaction

For a Suzuki-Miyaura coupling reaction, bromobenzene (0.2 mol, TOKYO CHEMICAL INDUSTRY CO., LTD.), phenylboronic acid (0.32 mol, TOKYO CHEMICAL INDUSTRY CO., LTD.), potassium carbonate (0.4 mol, WAKO-Chemicals, Ltd.), o-xylene (solvent, 560 ml, WAKO-Chemicals. Ltd.), tridecane (internal standard material), the precursor (0.5 mg, Pd: $1.9 \times 10^{-8}$ mol) as obtained in Example 9 were added to a three-neck flask as shown in FIG. 1. The reaction was carried out under an $N_2$ atmosphere in an oil bath at a temperature of 110° C. while stirring.

2. Experimental Results

In order to investigate effects of $H_2$ bubbling on the catalytic activity, the conversion rate of bromobenzene and the time change of the TON were compared between when the reaction was carried out without $H_2$ bubbling and when $H_2$ bubbling was carried out both before and during the reaction. The $H_2$ bubbling was carried out by flowing gas having 6% of hydrogen and 94% of argon at a rate of 30 mUmin. The $H_2$ bubbling before the reaction was performed at room temperature for 1 hour. The time change of the conversion rate of bromobenzene was analyzed with a capillary GC device equipped with an FID detector (Shimadzu 2010) by sampling a small amount of the solution with a fixed interval.

Figure 18:
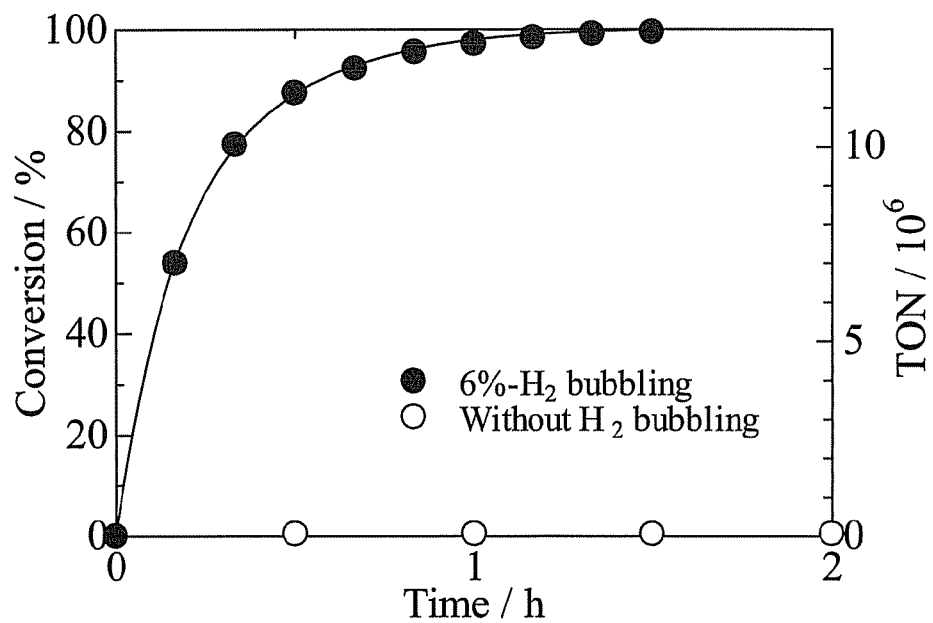
FIG. 18 is a graph showing an effect of $H_2$ bubbling according to Example 10.

FIG. 18 show the results obtained. As clearly demonstrated by referring to FIG. 18, the reaction hardly proceeded in the case of no $H_2$ bubbling, but the reaction proceeded at a very high rate in the case of carrying out $H_2$ bubbling. In addition, the TON reached 13,000,000. Since the TON of bromobenzene was 5,300,000 in Examples 1 to 8, two times or higher catalytic activity than that of Examples 1 to 8 was achieved in Example 10.

Example 11

Verification of Reduction of Precursor by $H_2$ Bubbling

Example 11 verifies that the $H_2$ bubbling under the conditions of Example 10 reduces a zeolite-palladium complex precursor as prepared in Example 9. For this verification, Pd $L_3$-edge XANES measurements were carried out while performing $H_2$ bubbling over the precursor as prepared in Example 9 under the conditions of Example 10. The XANES measurements were conducted using BL10 which was housed in Ritsumeikan University SR Center.

Figure 19:
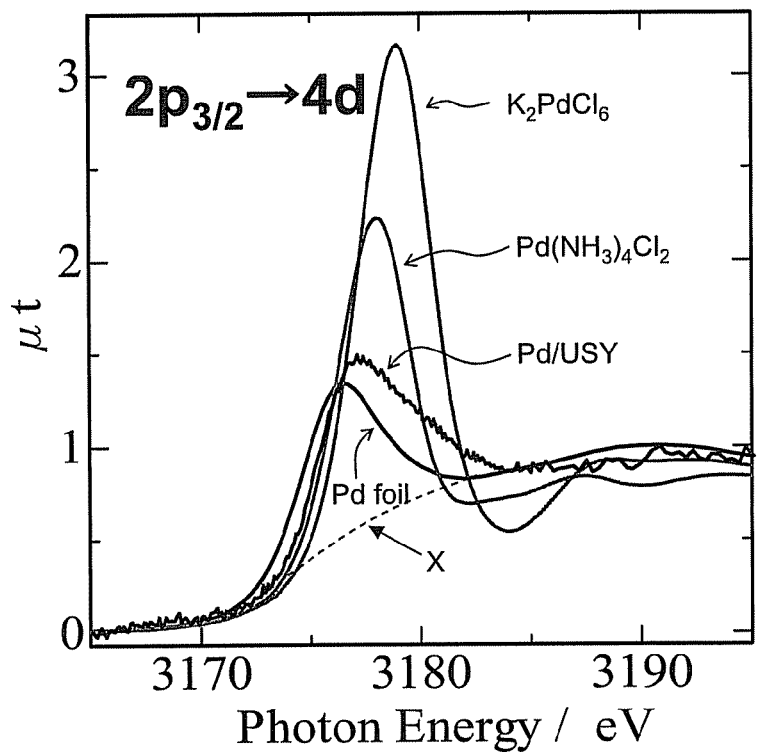
FIG. 19 shows XANES spectra at Pd $L_3$-edge so as to determine the oxidation number of Pd according to Example 11.
Figure 20:
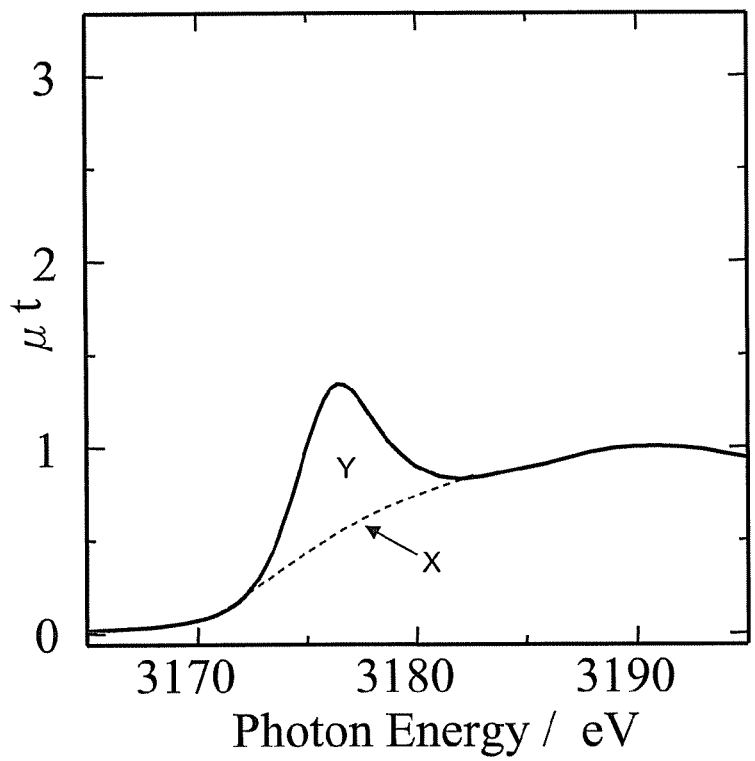
FIG. 20 is a plot to be used for explaining a procedure for calculating the oxidation number of Pd according to Example 11.

FIG. 19 shows the resulting spectra. The oxidation number was determined by using the following procedure. For each sample, the area of region Y located above a dotted line was calculated by smoothly drawing the line between before and after the peak like dotted line X as shown in FIG. 20.

It is known that: the oxidation number of Pd foil is 0; the oxidation number of $Pd(NH_3)_4Cl_2$ is 2; and the oxidation number of $K_2PdCl_6$ is 4. It is also known that the area and the oxidation number have a linear relationship. Therefore, determination of the area of Pd/USY determines the oxidation number of Pd/USY. When the oxidation number was calculated by the above method, the oxidation number of Pd/USY whose precursor had been reduced was +0.26, indicating that the precursor was found to be certainly reduced.

Example 12

Dependency on Reactants of Coupling Reaction

In Example 12, reactants of a coupling reaction were variously changed. A Suzuki-Miyaura coupling reaction was carried out under the same condition as Example 10 except that change. Table 7 shows the results.

As clearly demonstrated by referring to Table 7, the TON of various reactants was found to exhibit a very high value.

TABLE 7

| | Ar—Br + Ar'—B(OH)$_2$ → Ar—Ar' | | | | | |
|---|---|---|---|---|---|---|
| Entry | Ar—Br | Ar'—B(OH)$_2$ | Pd/ mol %$^b$ | Time/ h | Yield/ % | TON |
| 1 | ⌬—Br | ⌬—B(OH)$_2$ | $7.7 \times 10^{-6}$ | 1.5 | 99 | 13,000,000 |

TABLE 7-continued

Ar—Br + Ar'—B(OH)₂ → Ar—Ar'

| Entry | Ar—Br | Ar'—B(OH)₂ | Pd/ mol %[b] | Time/ h | Yield/ % | TON |
|---|---|---|---|---|---|---|
| 2 | H₃COC—C₆H₄—Br | C₆H₅—B(OH)₂ | $9.2 \times 10^{-6}$ | 1.5 | 99 | 11,000,000 |
| 3 | H₃C—C₆H₄—Br | C₆H₅—B(OH)₂ | $9.5 \times 10^{-6}$ | 3 | 96 | 11,000,000 |
| 4 | H₃CO—C₆H₄—Br | C₆H₅—B(OH)₂ | $1.3 \times 10^{-5}$ | 6 | 89 | 8,900,000 |
| 5 | H₂N—C₆H₄—Br | C₆H₅—B(OH)₂ | $5.0 \times 10^{-5}$ | 18 | 83 | 2,400,000 |
| 6 | 1-bromonaphthalene | C₆H₅—B(OH)₂ | $1.3 \times 10^{-4}$ | 1 | 99 | 760,000 |
| 7 | C₆H₅—Br | 1-naphthyl-B(OH)₂ | $2.2 \times 10^{-3}$ | 1 | 75 | 60,000 |
| 8 | H₃COC—C₆H₄—Br | 1-naphthyl-B(OH)₂ | $4.3 \times 10^{-4}$ | 1 | 99 | 230,000 |
| 9 | 1-bromonaphthalene | 1-naphthyl-B(OH)₂ | $9.2 \times 10^{-4}$ | 1 | 84 | 130,000 |
| 10 | 1-bromo-2-methylnaphthalene | 1-naphthyl-B(OH)₂ | $6.4 \times 10^{-3}$ | 1 | 78 | 20,000 |

Example 13

Effect of Support

Figure 21:
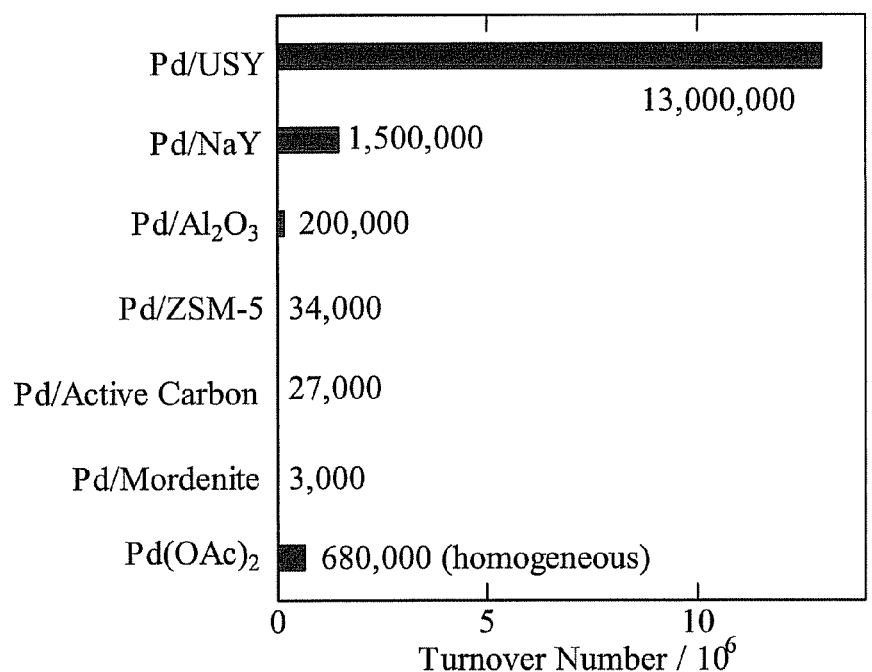
FIG. 21 is a graph indicating an effect of supports according to Example 13.

In Example 13, a support was variously changed. A Suzuki-Miyaura coupling reaction was carried out under the same condition as Example 10 except that change. FIG. 21 shows the results.

As clearly demonstrated by referring to FIG. 21, when the support was USY-zeolite, the catalytic activity was very high compared to that of the cases of using a support other than this.

Figure 22:
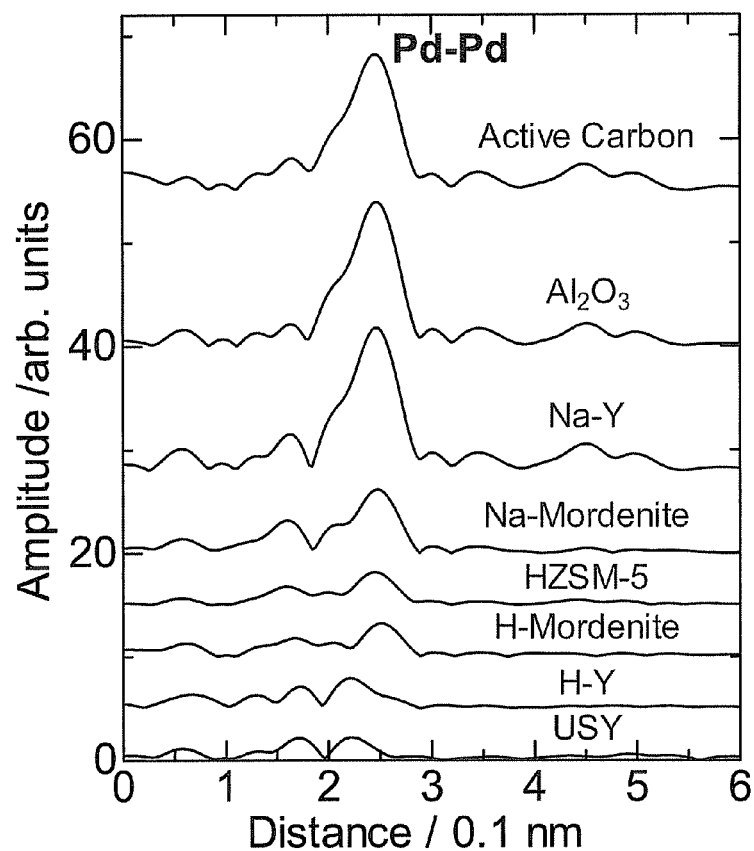
FIG. 22 shows spectra indicating dispersion states of Pd according to Example 13.

In addition, when the dispersion state of Pd was analyzed by a method similar to Example 4, spectra of FIG. 22 were obtained. As clearly demonstrated by referring to FIG. 22, when the support was USY-zeolite, no Pd—Pd peak was observed, indicating that Pd became an atomic state and dispersed.

Example 14

Effect of Conditions for Steaming Treatment

In Example 14, it was investigated what kinds of effects the conditions for steaming treatment for NH₄—Y-zeolite imparted on its catalytic activity.

Effect of Temperature of Steaming Treatment

The duration of steaming treatment was changed to 3 hours, and the treatment temperature was also variously changed. Except these changes, a zeolite-palladium complex precursor was prepared under the same condition as Example 9, and a Suzuki-Miyaura coupling reaction was carried out under the conditions of Example 10.

Figure 23:
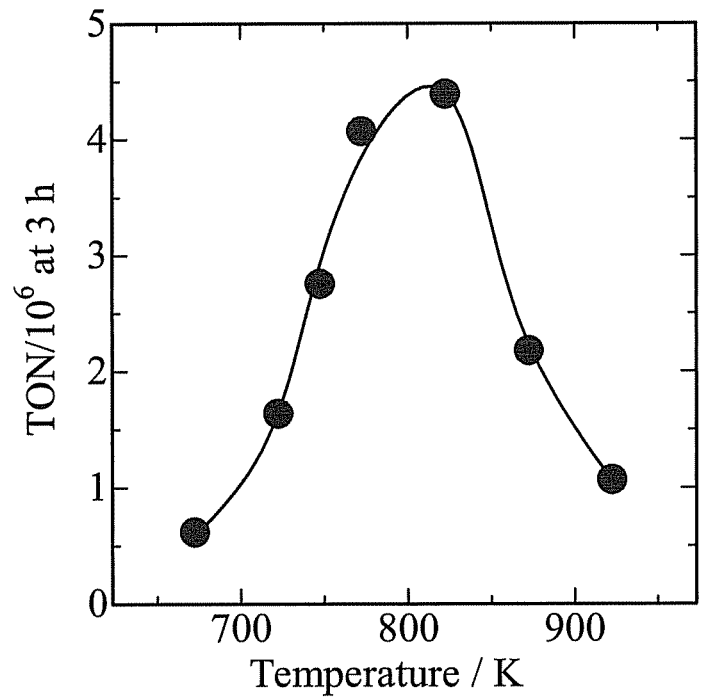
FIG. 23 is a graph indicating a relationship between a temperature of steaming treatment for $NH_4$—Y-zeolite and a TON according to Example 14.

FIG. 23 shows the results obtained. As clearly demonstrated by referring to FIG. 23, when the temperature was between 748 K (475° C.) and 873 K (600° C.), the catalytic activity was high. In the case of 823 K (550° C.), the maximal catalytic activity was found to be achieved.

Figure 24:
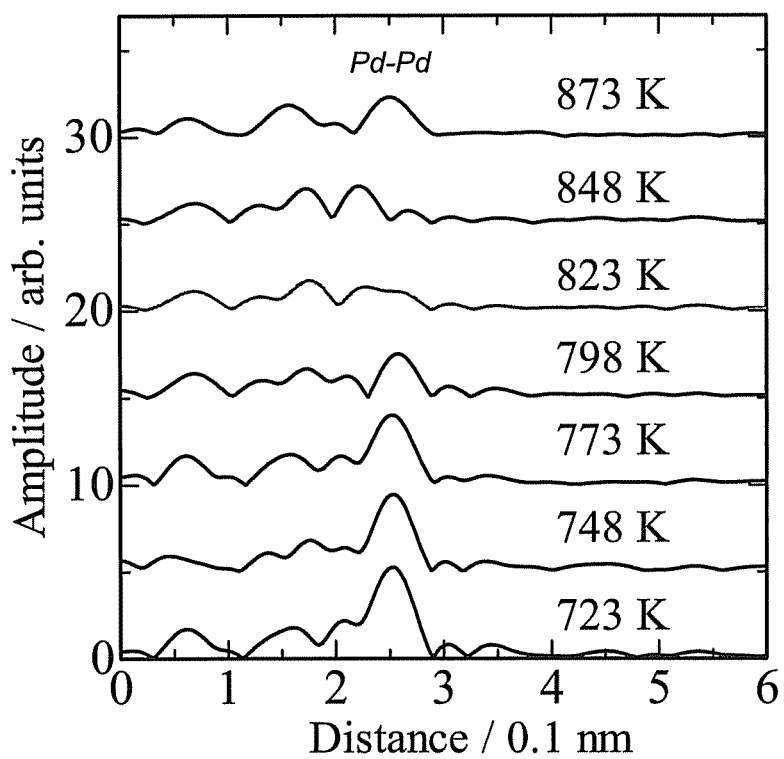
FIG. 24 shows spectra indicating dispersion states of Pd when steaming treatment for $NH_4$—Y-zeolite was carried out at various temperatures according to Example 14.

In addition, when the dispersion state of Pd was analyzed by a method similar to Example 4, the spectra of FIG. 24 were obtained. As clearly demonstrated by referring to FIG. 24, when the temperature of steaming treatment was 823 K, no Pd—Pd peak was observed, indicating that Pd became an atomic state and dispersed.

Effect of Duration of Steaming Treatment

The duration of steaming treatment was variously changed. Except that, a zeolite-palladium complex precursor was prepared under the same condition as Example 9, and a Suzuki-Miyaura coupling reaction was carried out under the conditions of Example 10.

Figure 25:
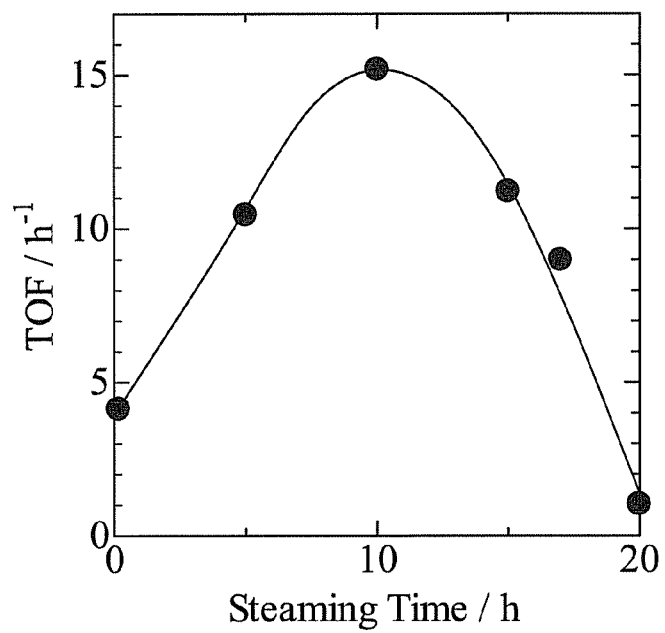
FIG. 25 is a graph indicating a relationship between a temperature of steaming treatment for $NH_4$—Y-zeolite and a TOF according to Example 14.

FIG. 25 shows the results obtained. As clearly demonstrated by referring to FIG. 25, when the duration of steaming treatment was between 5 and 17 hours, the catalytic activity was high. In the case of 10 hours, the maximal catalytic activity was found to be achieved.

Effect of Water Vapor Partial Pressure

The duration of steaming treatment was changed to 1 hour, and the water vapor partial pressure was changed to 40%. Except these changes, a zeolite-palladium complex precursor was prepared under the same condition as Example 9, and a Suzuki-Miyaura coupling reaction was carried out under the conditions of Example 10.

As a result, the TOF was 4,900,000/hour. As described below, when a precursor as obtained under the conditions of Example 9 was used, the TOF was about 15,000,000/hour. Accordingly, while the catalytic activity was lower than this, the effects of the water vapor partial pressure were found to be not so large.

Occurrence of Strong Acid Sites by Steaming Treatment

H—Y-zeolite and H—USY-zeolite as obtained by performing steaming treatment under various conditions were analyzed by an IRMS-TPD method. This analysis was conducted by using the following procedure.

4.1. Analysis by IRMS-TPD Method

Figure 26:
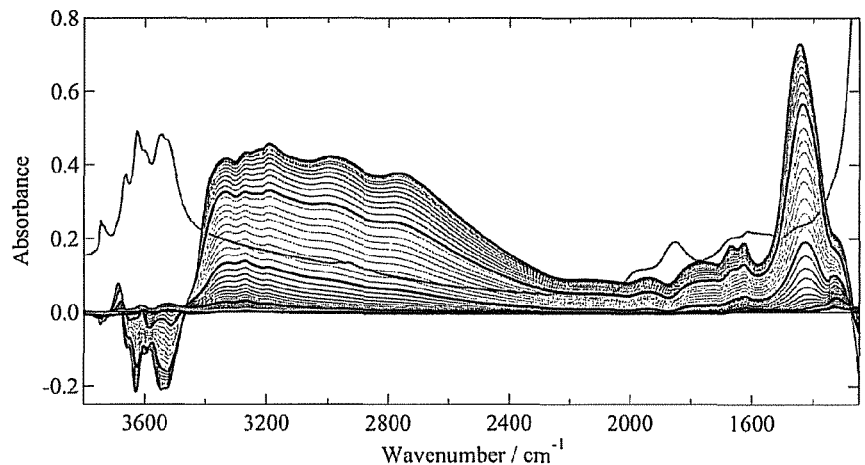
FIG. 26 shows difference spectra by IR-TPD so as to illustrate an analysis procedure by an IRMS-TPD method according to Example 14.

First, $NH_3$ was made to be absorbed on H—USY-zeolite at 373 K and 13 kPa, followed by exhausting the gas phase $NH_3$ for 30 minutes. Next, IR spectra of H—USY-zeolite (see, FIG. 26) were determined while elevating a temperature at a rate of 10 $Kmin^{-1}$. Then, the band responsible for the bending vibration of $NH_4^+$ near 1430 $cm^{-1}$ was quantified every 10 K. In addition, the band near 1325 $cm^{-1}$ (i.e., $NH_3$ which was absorbed on Lewis acid) was also quantified every 10 K. The differential change in the area at temperatures was determined, and the IR TPD spectra for adsorbed species were obtained. The respective IR-TPD spectra (adsorbed species) were multiplied by a coefficient corresponding to the inverse number of an absorbance coefficient (the ratio was kept constant: $NH_4^+$ (1430 $cm^{-1}$):$NH_3$ (1325 $cm^{-1}$)=1: 2.15). The sum of them was made to correspond to spectra obtained with a mass spectrometer (MS).

The OH region of IR difference spectra at the respective temperatures was subjected to waveform separation into a band near 3633 $cm^{-1}$ derived from OH present in a supercage, a band near 3609 $cm^{-1}$ derived from AlOH outside a framework, a band near 3598 $cm^{-1}$ derived from USY-specific strong acid sites (O1H), a band near 3551 $cm^{-1}$ derived from a sodalite cage, and a band near 3520 $cm^{-1}$ derived from a hexagonal prism. Then, the differential change in the area at temperatures was calculated, and the IR-TPD spectra for OH were obtained.

Figure 27:
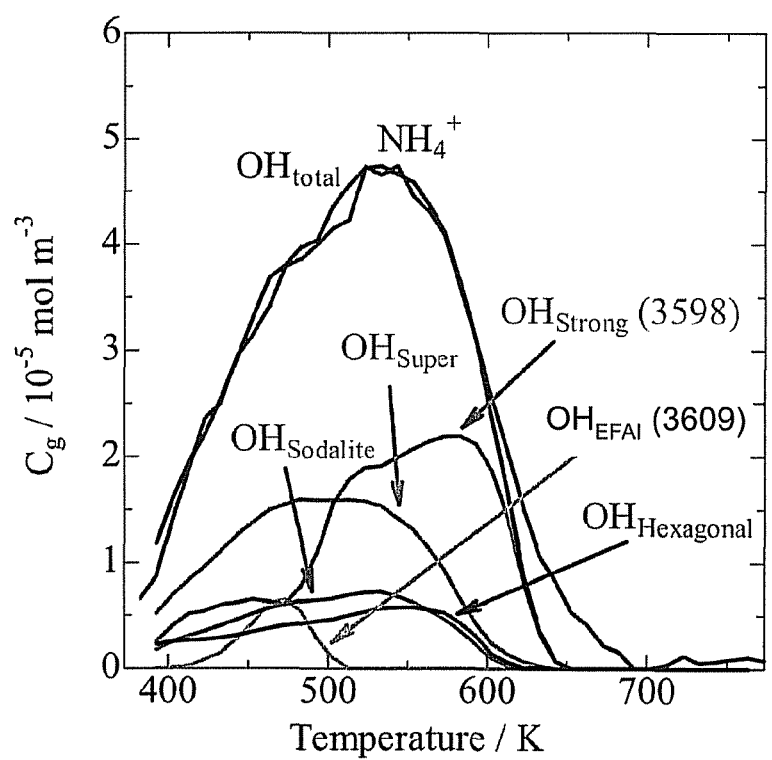
FIG. 27 shows IR-TPD spectra so as to illustrate an analysis procedure by an IRMS-TPD method according to Example 14.

The respective IR-TPD spectra (OH) were multiplied by a negative coefficient corresponding to the inverse number of an absorbance coefficient (the ratio was kept constant: $OH_{super}$:$OH_{EFAl}$:$OH_{strong}$:$OH_{sodalite}$:$OH_{hexagonal}$=1.0:2.7:2.7:0.38:0.38). The sum of them was made to correspond to $NH_4^+$ IR-TPD spectra (see, FIG. 27).

The IR-TPD spectra were determined for each OH in such a manner, and the acid content and acid strength for each OH were quantified by using a theoretical formula. The acid strength $\Delta H$ of the strong acid sites was 133 kJ/mol.

4-2. IR Difference Spectra of IR-TPD as Obtained by IRMS-TPD Method

Figure 28:
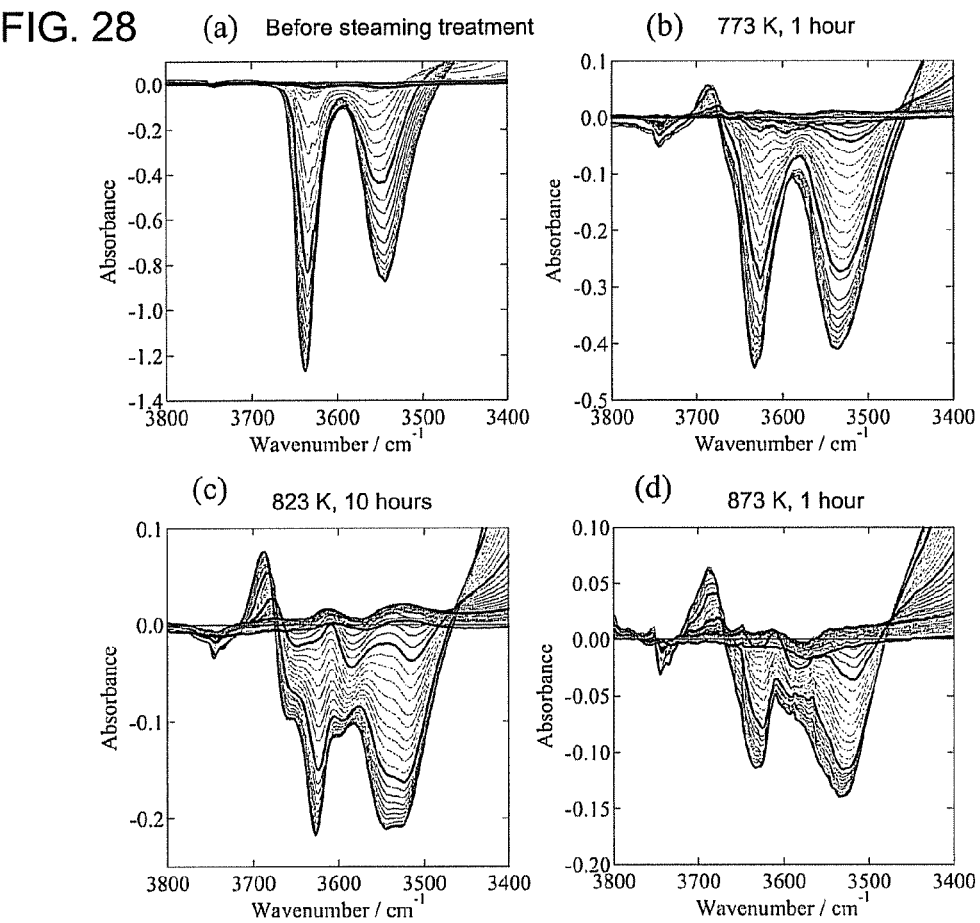
FIG. 28 is magnified views of the OH bands of the IR difference spectra by IR-TPD according to Example 14.

FIG. 28 shows the results. FIG. 28(a) corresponds to H—Y-zeolite. FIG. 28(b) corresponds to that with steaming treatment at 773 K for 1 hour. FIG. 28(c) corresponds to that with steaming treatment at 823 K for 10 hours. FIG. 28(d) corresponds to that with steaming treatment at 873 K for 1 hour.

As clearly demonstrated by referring to FIGS. 28(a) to (d), the peak of an acidic OH group (strong acid sites) which was strengthened by an inductive effect due to an Al species outside a framework was found to be maximal in FIG. 28(c). In addition, for the spectra of FIG. 28(a) in which steaming treatment was not carried out, no peak of the strong acid sites was substantially observed, indicating the peak of the strong acid sites was found to appear by steaming treatment. Further, in the spectra of FIG. 28(d) in which steaming treatment was carried out at 873 K, a peak of the strong acid sites was found to be smaller than that of FIG. 28(c). This indicates that if the temperature of steaming treatment is too high, the peak of the strong acid sites becomes small.

4-3. Relationship between Amount of Strong Acid Sites and Catalytic Activity

A relationship was investigated between the amount of strong acid sites in H—USY-zeolite and the TOF when a Suzuki-Miyaura coupling reaction was carried out under the conditions of Example 10 by using a zeolite-palladium complex precursor as obtained using this zeolite.

Figure 29:
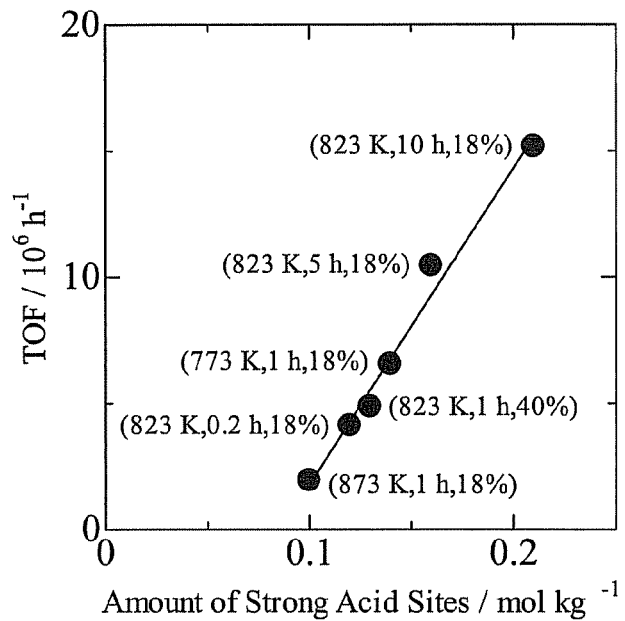
FIG. 29 is a graph indicating a relationship between the number of strong acid sites and a TON according to Example 14.

FIG. 29 shows the results. As clearly demonstrated by referring to FIG. 29, as the amount of strong acid sites becomes larger, the TOF is found to lineally increase. This result strongly suggests that the presence of strong acid sites correlates with the catalytic activity. Acid sites other than the strong acid sites and the TOF were examined as to whether or not a correlation similar to FIG. 29 was present. However, the TOF failed to correlate with the acid sites other than the strong acid sites. The reason is not necessarily clear why the number of strong acid sites correlates with the TOF. However, the strong acid sites seem to contribute to stabilization of Pd in an atomic state or in a microcluster state.

The invention claimed is:

1. A method for producing a zeolite-palladium complex, comprising the step of carrying out $H_2$ bubbling over a zeolite-palladium complex precursor, as obtained by mixing $NH_4^+$-containing USY-zeolite with a palladium ammonium salt, in a solvent containing at least one of xylene and toluene at a temperature between 20° C. and 170° C. under an $H_2$ partial pressure of 1 to 30%.

2. The method according to claim 1, wherein an amount of $NH_4^+$ in the $NH_4^+$-containing USY zeolite is between 0.15 and 1.3 mol/kg.

3. The method according to claim 1, wherein the $NH_4^+$-containing USY-zeolite is produced by ion exchange of H—USY-zeolite with an ammonium salt, followed by calcination.

4. The method according to claim 3, wherein an amount of strong acid sites having ΔH of 130 to 145 kJ/mol in the H—USY-zeolite is 0.12 mol/kg or more.

5. The method according to claim 3, wherein the calcination is carried out at 150 to 350° C.

* * * * *